(12) United States Patent
Kyu et al.

(10) Patent No.: US 9,062,022 B2
(45) Date of Patent: Jun. 23, 2015

(54) POLYMER COMPOSITION AND DIALYSIS MEMBRANE FORMED FROM THE POLYMER COMPOSITION

(75) Inventors: Thein Kyu, Akron, OH (US); Neelakandan Chandrasekaran, Woodbury, MN (US)

(73) Assignee: The University of Akron, Akron, OH (US)

(*) Notice: Subject to any disclaimer, the term of this patent is extended or adjusted under 35 U.S.C. 154(b) by 897 days.

(21) Appl. No.: 13/132,431

(22) PCT Filed: Dec. 1, 2009

(86) PCT No.: PCT/US2009/066166
§ 371 (c)(1),
(2), (4) Date: Jun. 3, 2011

(87) PCT Pub. No.: WO2010/065484
PCT Pub. Date: Jun. 10, 2010

(65) Prior Publication Data
US 2011/0233138 A1    Sep. 29, 2011

Related U.S. Application Data

(60) Provisional application No. 61/119,822, filed on Dec. 4, 2008.

(51) Int. Cl.
*B01D 61/24* (2006.01)
*B01D 61/28* (2006.01)
*C07D 311/86* (2006.01)
*B01D 71/44* (2006.01)
*B01D 71/56* (2006.01)

(Continued)

(52) U.S. Cl.
CPC .......... *C07D 311/86* (2013.01); *Y10T 29/49826* (2015.01); *B01D 61/243* (2013.01); *B01D 71/44* (2013.01); *B01D 71/56* (2013.01); *B01D 71/68* (2013.01); *A61M 1/16* (2013.01); *B01D 2323/39* (2013.01); *B01D 2325/48* (2013.01)

(58) Field of Classification Search
USPC .................. 29/428; 210/500.21, 500.23, 646; 524/109, 110; 549/392
See application file for complete search history.

(56) References Cited

U.S. PATENT DOCUMENTS

| 4,456,746 A | 6/1984 | Horner |
| 4,722,795 A | 2/1988 | Gohl et al. |

(Continued)

FOREIGN PATENT DOCUMENTS

| EP | 0 870 133 | 6/1997 |
| GB | 1576228 A | 10/1980 |
| WO | WO 03/006134 | 1/2003 |

OTHER PUBLICATIONS

Peterson, G., "Evaluation of the Biochemical Targets of Genistein in Tumor Cells", American Institute of Nutrition, 1995, pp. 784S-789S.

(Continued)

*Primary Examiner* — Dirk Bass
(74) *Attorney, Agent, or Firm* — Renner Kenner Greive Bobak Taylor & Weber

(57) ABSTRACT

A biocompatible polymer composition suited to forming a dialysis membrane includes a matrix material and at least one xanthone. The composition may be formed into a membrane for inserting into a dialyzer filter whereby free radicals in the fluid are removed by the membrane.

27 Claims, 13 Drawing Sheets

(51) Int. Cl.
B01D 71/68 (2006.01)
A61M 1/16 (2006.01)

(56) References Cited

U.S. PATENT DOCUMENTS

| | | | |
|---|---|---|---|
| 4,933,084 A | 6/1990 | Bandel et al. | |
| 4,935,141 A | 6/1990 | Buck et al. | |
| 5,152,894 A | 10/1992 | Haubs et al. | |
| 5,505,851 A | 4/1996 | Wagener et al. | |
| 5,762,798 A | 6/1998 | Wenthold et al. | |
| 5,911,880 A | 6/1999 | Klein et al. | |
| 5,938,929 A | 8/1999 | Shimagaki et al. | |
| 6,001,288 A * | 12/1999 | Saruhashi et al. | 264/41 |
| 6,017,455 A | 1/2000 | Shimoda et al. | |
| 6,329,422 B1 | 12/2001 | Fischer et al. | |
| 6,382,526 B1 | 5/2002 | Reneker et al. | |
| 6,520,425 B1 | 2/2003 | Reneker | |
| 6,958,156 B2 | 10/2005 | Hendler et al. | |
| 6,994,788 B1 | 2/2006 | Dyck et al. | |
| 7,320,797 B2 | 1/2008 | Gupta | |
| 7,358,288 B2 | 4/2008 | Kerres | |
| 2002/0055644 A1 | 5/2002 | Winter et al. | |
| 2005/0244647 A1 | 11/2005 | Droschel et al. | |
| 2006/0165798 A1 | 7/2006 | Edgren et al. | |
| 2007/0163950 A1* | 7/2007 | Wechs | 210/500.41 |
| 2007/0207179 A1 | 9/2007 | Anderson et al. | |
| 2008/0000830 A1 | 1/2008 | Mabuchi et al. | |
| 2008/0142442 A1 | 6/2008 | Steiger et al. | |

OTHER PUBLICATIONS

Verdrengh, M., et al. "Genistein as an anti-inflammatory agent", Inflamm.res. 52 (2003) 341-346.
Xu, J., et al. "Genistein Inhibits Expressions of NADPH Oxidase p22phox and Angiotensin II Type 1 Receptor in Aortic Endothelial Cells from Stroke-Prone Spontaneously Hypertensive Rats", Hypertens Res, 2004, vol. 27, No. 9, pp. 675-683.
Dar, et al.; Analgesic and Antioxidant Activity of Mangiferin and Its Derivatives: the Structure Activity Relationship; Biol. Pharm. Bull. 28(4) 596-600 vol. 28, No. (2005).
Extended European Search Report, EP App. No. 09830941.2, (2013).
Bloch, et al. "Position of The American Dietetic Association: Phytochemicals and functional foods," Journal of the American Dietetic Association, Apr. 1995, vol. 95, No. 4.
Chandrasekaran, et al. "Miscibility Characterization in Relation to Phase Morphology of Poly(ether sulfone)/Poly(vinyl pyrrolidone) Blends Containing a Phytochemical," J. Phys. Chem. B 2009, 113, 8520-8526.
Chandrasekaran, et al. "Hydrogen bonding interactions and miscibility studies of poly(amide)/poly-(vinyl pyrrolidone) blends containing mangiferin," Polymer 50 (2009) 2885-2892.
Garrido, et al. "In vivo and in vitro anti-inflammatory activity of Mangifera indica L. extract (VIMANG®)," Pharmacological Research 50 (2004) 143-149.
Descamps-Latscha, et al. "Dialysis-Induced Oxidative Stress: Biological Aspects, Clinical Consequences, and Therapy," Seminars in Dialysis, vol. 14, No. 3 (May-Jun.) 2001, pp. 160-162.
Galli, et al. "Oxidant Stress in Hemodialysis," Nephron 2000;84:1-5.
Leiro, et al. "In vitro effects of mangiferin on superoxide concentrations and expression of the inducible nitric oxide synthase, tumour necrosis factor-α and transforming growth factor-β genes" Biochemical Pharmacology 65 (2003) 1361-1371.
Leiro, et al. "Expression profiles of genes involved in the mouse nuclear factor-kappa B signal transduction pathway are modulated by mangiferin," International Immunopharmacology 4 (2004) 763-778.
Pinto, et al. "Xanthone Derivatives: New Insights in Biological Activities," *Current Medicinal Chemistry*, 2005, 12, 2517-2538.
Rodriguez, et al. "Effects of a natural extract from L, and its active compound, mangiferin, on energy state and lipid peroxidation of red blood cells," Biochimica et Biophysica Acta 1760 (2006) 1333-1342.
Sasaki, et al. "Development of vitamin E-modified polysulfone membrane dialyzers," J Artif Organs (2006) 9:50-60.
Tang, et al. "Characterizaton of Antioxidant and Antiglycation Properties and Isolation of Active Ingredients From Traditional Chinese Medicines," Free Radical Biology & Medicine, vol. 36, No. 12, pp. 1575-1587, 2004.
Ward, et al. "What Clinically Important Advances in Understanding and Improving Dialyzer Function Have Occurred Recently?" Seminars in Dialysis. vol. 14, No. 3 (May-Jun.) 2001, pp. 160-162.
Braune, et al. "Deglycosylation of puerarin and other aromatic C-glucosides by a newly isolated human intestinal bacterium," Environmental Microbiology, vol. 13, Issue 2, pp. 482-494, Feb. 2011— abstract only.
Canestrari, et al. "Redox state, antioxidative activity and lipid peroxidation in erythrocytes and plasma of chronic ambulatory peritoneal dialysis patients," Clinica Chimica Acta 234 (1995) 127-136.
Chandrasekaran, et al. "Miscibility Studies on Polymer Blends Modified with Phytochemicals," American Physical Society, Mar. 16-20, 2009—abstract only.
Chandrasekaran, et al. "Hydrogen bonding interactions and miscibility studies of poly(amideypoly(vinyl pyrrolidone) blends containing mangiferin," Polymer 50 (2009) 2885-2892.
Garcia, et al. "Modulation of rat macrophage function by the *Mangifera indica* L. extracts Vimang and mangiferin," International Immunopharmacology 2 (2002) 797-806.
Hench, et al. "Third-Generation Biomedical Materials," *Science* 295, 1014 (2002).
Herbelin, et al. "Influence of uremia and hemodialysis on circulating interleukin-1 and tumor necrosis factor α," *Kidney International*, vol. 37 (1990), pp. 116-125.
Kimmel, et al. "Immunologic function and survival in hemodialysis patients," *Kidney International*, vol. 54, 1998, pp. 236-244.
Miesel, et al. "Priming of NADPH Oxidase by Tumor Necrosis Factor Alpha in Patients with Inflammatory and Autoimmune Rheumatic Diseases," *Inflammation*, vol. 20, No. 4, 1996.
Miura, et al. "Antidiabetic activity of a xanthone compound, mangiferin," Phytomedicine. vol. 8(2), pp. 85-87, Mar. 2001.
Mohanty, et al. "Glucose Challenge Stimulates Reactive Oxygen Species (ROS) Generation by Leucocytes," Journal of Clinical Endocrinology & Metabolism, 2000, 85: 2970-2973.
Nilsson, et al. "The role of complement in biomaterial-induced inflammation," Molecular Immunology 44 (2007) 82-94.
Parikh, et al. "IL-6 Production in Human Intestinal Epithelial Cells Following Stimulation with IL-1β Is Associated with Activation of the Transcription Factor NF-κB[1,]" Journal of Surgical Research, 69, 139-144 (1997).
Ratner, et al. "Biomaterials: Where We Have Been and Where We Are Going," Annu. Rev. Biomed. Eng., 2004, 6:41-75.
Sánchez, et al. "Protective Effects of *Mangifera indica* L. Extract, Mangiferin and Selected Antioxidants Against TPA-Induced Biomolecules Oxidation and Peritoneal Macrophage Activation in Mice," Pharmacological Research, vol. 42, No. 6, 2000.
Sarkar, et al. "βR-D-Glucoside Suppresses Tumor Necrosis Factor-induced Activation of Nuclear Transcription Factor κB but Potentiates Apoptosis," The Journal of Biological Chemistry, vol. 279, No. 32, Issue of Aug. 6, pp. 33768-33781, 2004.
Schindler, et al. "Transcription, not synthesis, of interleukin-1 and tumor necrosis factor by complement," *Kidney International*, vol. 37 (1990), pp. 85-93.

* cited by examiner

POLYMER COMPOSITION AND DIALYSIS MEMBRANE FORMED FROM THE POLYMER COMPOSITION

This application claims the benefit of International Application PCT/US09/66166, filed Dec. 1, 2009, entitled POLYMER COMPOSITION AND DIALYSIS MEMBRANE FORMED FROM THE POLYMER COMPOSITION, by Neelakandan Chandrasekaran and Thein Kyu, and of U.S. Application Ser. No. 61/119,822, filed on Dec. 4, 2008, entitled POLYMER COMPOSITION AND DIALYSIS MEMBRANE FORMED FROM THE POLYMER COMPOSITION, by Neelakandan Chandrasekaran and Thein Kyu, from which PCT/US09/66166 claims the benefit, the disclosures of all of which are incorporated herein in their entireties, by reference.

BACKGROUND OF THE DISCLOSURE

The exemplary embodiment relates to a biocompatible polymer composition which includes an antioxidant, such as a xanthone. It finds particular application in forming dialysis membranes, and will be described with particular reference thereto. However, it is to be appreciated that the present exemplary embodiment is also amenable to other like applications.

Currently, a variety of surface modification techniques are available to produce biocompatible materials. They include polyethylene glycol grafting, albumin coatings, phospholipid mimicking surfaces, plasma treatments, fluorination, modification using anti-platelet agents like prostacyclin and fibrinolytic agents, and heparinizing the surface. Anti-bacterial surface treatments have also been proposed.

However, these existing biocompatible materials may only offer a few additional properties over their basic functional requirements. Medical applications such as implants, hemodialysis, peritoneal dialysis, and other similar applications, would benefit from multiple properties, such as anti-bacterial, anti-viral, anti-oxidative, and/or anti-inflammatory properties in order to maintain a better quality of life for a patient.

As an example, hemodialysis is primarily used to provide an artificial replacement for lost kidney function by filtering impurities from the blood. However, there are problems associated with hemodialysis, such as an increase in oxidants in the blood and inflammatory responses due to long term exposure of the blood to a synthetic polymer surface. At this time, in order to obtain relief, a dialysis patient generally undergoes supplemental drug therapy which adds a significant cost to the overall dialysis costs.

Recently, concerns have been expressed over a series of pathologic events deriving from reactive oxygen species (ROS). This is so called "oxidative stress" which is further exacerbated during dialysis due to the reduction of antioxidants and interactions between blood and the dialysis membrane. Oxidative stress is the result of an imbalance between pro- and antioxidant molecules. Some hemodialysis membranes now utilize vitamin-E in order to provide anti-oxidant properties. However, inflammatory responses still occur with such membranes.

The exemplary embodiment provides a biocompatible polymer composition suited to use in hemodialysis as a membrane for insertion into a dialyzer filter which overcomes the above-referenced problems, and others.

BRIEF DESCRIPTION OF THE DISCLOSURE

In accordance with one aspect of the exemplary embodiment, a biocompatible polymer composition includes a matrix material, and at least one antioxidant, such as a xanthone.

The matrix material may be selected from the group consisting of polysulfones, polyamides, polyvinylpyrrolidones, polycarbonates, polysulfones, polyacrylonitriles, and combinations thereof. The polysulfone may be a polyethersulfone.

The matrix material may comprise a blend. The blend may include a polyvinylpyrrolidone and a thermoplastic polymer. The thermoplastic polymer may include at least one of a polyamide and a polyethersulfone.

In various aspects, the at least one of a polyamide and a polyethersulfone may constitute from 5-95% by weight of the blend. The at least one of a polyamide and a polyethersulfone may constitute at least 40% by weight of the blend or at least 50% by weight of the blend.

The xanthone of the composition may include a hydroxylated xanthone.

The xanthone may have a structure represented by Structure 11:

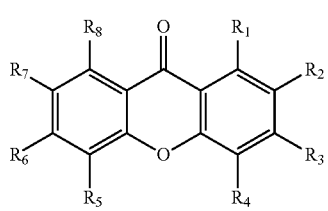

Structure 11 where $R_1$, $R_2$, $R_3$, $R_4$, $R_5$, $R_6$, $R_7$, and $R_8$ are independently selected from H, OH and glycosyl and at least one of $R_1$, $R_2$, $R_3$, $R_4$, $R_5$, $R_6$, $R_7$, and $R_8$ includes an OH.

The xanthone may comprise an isolated naturally occurring xanthone.

The xanthone may include a glycosylated xanthone. The glycosylated xanthone may include 1,3,6,7-tetrahydroxyxanthone-C2-β-D-glycoside (mangiferin).

The xanthone may include a non-glycosylated xanthone which may be selected from the group consisting of 1,3,6,7-tetrahydroxyxanthone, 1,3-dihydroxyxanthone, 1,6-dihydroxyxanthone, 1,3,7-trihydroxyxanthone, 1,3,5,6-tetrahydroxyxanthone, 2,3,6,7-tetrahydroxyxanthone, 3,4,5,6-tetrahydroxyxanthone, and combinations thereof.

The xanthone may constitute at least 1% by weight of the polymer composition. The xanthone may constitute at least 10% by weight of the polymer composition. The xanthone may constitute up to 40% by weight of the polymer composition.

The xanthone may constitute up to 60% by weight of the polymer composition when the matrix material includes a polyethersulfone.

The xanthone may be dispersed throughout the matrix material.

In one aspect, a semi-permeable membrane includes the biocompatible polymer composition as described in any of the aspects above.

The membrane may be in the form of at least one of a thin film and fibers. The membrane may include a bundle of hollow fibers. The hollow fibers may each include a continuous hollow cavity, an outer wall surface which forms an outer side of the fiber, and an inner wall surface which defines the limits of the continuous hollow cavity. A wall thickness measured between the outer wall surface and the inner wall surface of the hollow fiber may be up to 100 μm.

In one aspect, a dialyzer filter includes a housing which houses the membrane as described in any of the aspects above.

In another aspect, a method of forming a dialyzer filter includes forming a membrane from the polymer composition, and inserting the membrane into a housing of the dialyzer filter.

In another aspect, a method of removing free radicals from a fluid includes filtering a fluid with the membrane, whereby free radicals in the fluid are removed by the above-described membrane.

In another aspect, a method for hemodialysis and/or hemofiltration includes contacting blood with a hollow fiber membrane comprising the biocompatible composition as described in any of the aspects above.

In another aspect, a method of forming a biocompatible polymer composition includes combining a matrix material for forming a polymer matrix and at least one xanthone to form a mixture.

In the method, the matrix material may be one which is miscible with the xanthone.

The blending of the matrix material and at least one xanthone may be carried out in the presence of a solvent. The solvent may be at least one of dimethylsulfoxide, dimethyl acetamide, and dimethyl formamide. The solvent may be dimethylsulfoxide.

The blending may include combining the matrix material, xanthone, and a solvent to form a liquid blend. The matrix material and xanthone may together constitute from 1-25% by weight of the liquid blend. The matrix material and xanthone may together constitute at least 5% by weight of the liquid blend. The matrix material and xanthone may together constitute at least 10% by weight of the liquid blend.

The method may further include immersing the liquid blend into a non-solvent to solidify the biocompatible polymer. The non-solvent may include water.

In another aspect, the method may include evaporation of the solvent.

The method may further include forming fibers from the liquid blend by at least one of electrospinning, a gas jet method, and solution spinning. The fibers may be hollow.

In another aspect, a biocompatible polymer composition consists essentially of polyvinylpyrrolidone, at least one of a polyamide and a polyethersulfone, and at least one hydroxylated xanthone.

In yet another aspect, a biocompatible polymer composition includes a matrix material and at least one anti-oxidant, wherein the anti-oxidant may include a hydroxylated xanthone.

DETAILED DESCRIPTION OF THE DISCLOSURE

Figure 1:
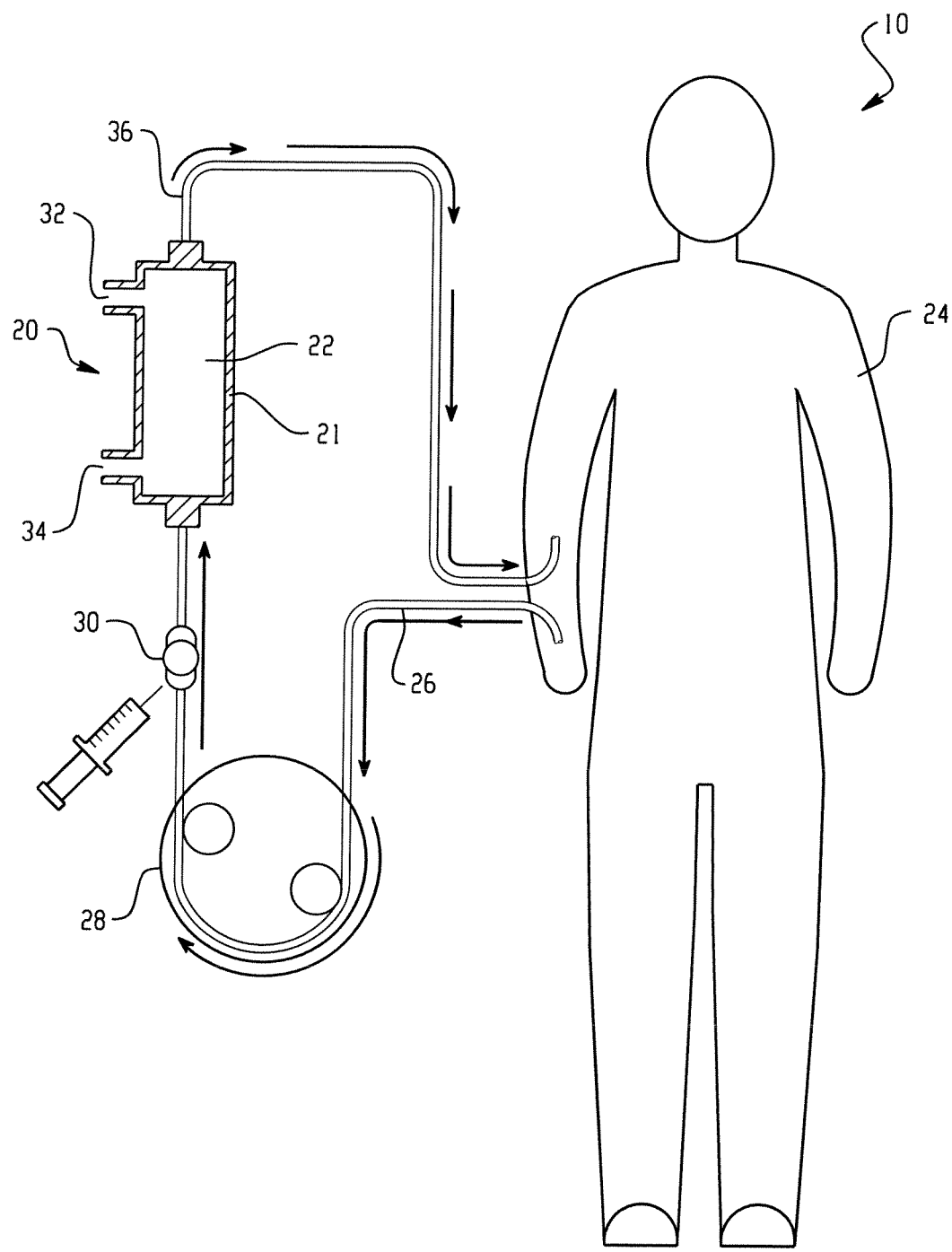
FIG. 1 is a schematic view of a hemodialysis circuit including a dialyzer filter containing an exemplary semi-permeable membrane formed from a biocompatible polymer composition.

Aspects of the exemplary embodiment relate to a biocompatible polymer composition, a membrane formed therefrom, a dialysis filter incorporating the membrane and/or other components formed from the polymer, a method of forming membranes from the polymer composition and to a method for reducing free radicals in a liquid, such as blood.

As used herein, the word polymer refers to homopolymers formed from a single monomer as well as copolymers formed from more than one monomer, block copolymers, polymer blends held together by ionic and/or weaker forms of bonding, and functionalized polymers. The exemplary biocompatible polymer composition may have various properties, such as antioxidant, anti-inflammatory, and antimicrobial properties. The polymer composition finds application in hemodialysis, such as in a dialysis membrane, in which the biocompatible polymer composition may act as a scavenger for free radicals and peroxides. The exemplary composition can thus help to reduce dialysis-induced-oxidative stress, a long term problem associated with hemodialysis.

The exemplary polymer composition is also biocompatible. By "biocompatible" it is meant that the composition is compatible with blood or may perform useful functions within the human body without having toxic or injurious effects.

The Biocompatible Polymer Composition

The biocompatible polymer composition includes a polymer matrix material and at least one antioxidant, such as a xanthone. Naturally occurring xanthones are biologically active plant phenols or polyphenols found in a few select tropical plants. When incorporated in the exemplary polymer composition, the xanthone exhibits strong antioxidant activity. The xanthone in the composition is able to maintain this activity, which is useful for inactivating free radicals in the blood or body. The exemplary xanthone(s) can be isolated, naturally occurring xanthone(s), or synthesized xanthone(s).

In comparison to existing membranes formed from Vitamin E, the exemplary membrane containing a xanthone is not only capable of providing antioxidant properties but may also provide the polymer composition with one or more other unique properties such as: anti-inflammation, anti-bacterial, anti-viral, anti-diabetic, and/or non-thrombogenic properties, immunomodulatory properties as related to the reduction on the expression of inflammation-related genes, and inhibition of platelet aggregation, reduced complement activation, and combinations thereof.

Exemplary xanthones which may be used in the polymer composition are a class of compounds which are derivatives of 9-oxo-xanthene (xanthone) as represented by Structure 1:

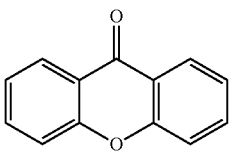

Structure 1

In one embodiment, the xanthone is a hydroxylated xanthone which includes at least one hydroxyl group or hydroxyl-containing group. The xanthone can be a glycosylated xanthone or a non-glycosylated xanthone. A glycosyl group can be derived from a cyclic form of glucose by removal of the hemiacetal hydroxyl group. A glycosylated xanthone includes at least one such glycosyl group.

Mangiferin is an exemplary glycosylated xanthone represented by the following Structure 2:

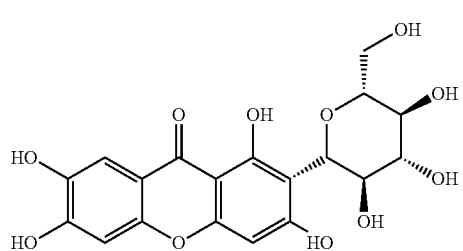

Structure 2

In Mangiferin, the glycosyl group located at the C-2 position is represented by Structure 3:

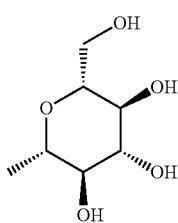

Structure 3

Mangiferin is a naturally occurring glycosylated xanthone which can be obtained from barks, leaves and fruits of *Mangifera indica* (Mango Tree). However, it is also anticipated that a synthetic form of mangiferin may be used. It has a molecular weight of 422.35 grams/mole, and melts at 271° C. When present in the polymer composition, it is able to provide the composition with some or all of anti-oxidant, anti-tumor, anti-viral, anti-bacterial, anti-fungal, anti-platelet, anti-thrombotic, anti-inflammatory, immunomodulatory and anti-diabetic properties.

When present in the composition, mangiferin has the ability to scavenge free radicals involved in lipid peroxidation initiation, an activity evidenced by redox properties.

Examples of non-glycosylated xanthones are represented by the following structures: 1,3,6,7-tetrahydroxyxanthone (norathyriol) (Structure 4), 1,3-dihydroxyxanthone (Structure 5), 1,6-dihydroxyxanthone (Structure 6), 1,3,7-trihydroxyxanthone (Structure 7), 1,3,5,6-tetrahydroxyxanthone (Structure 8), 2,3,6,7-tetrahydroxyxanthone (Structure 9), and 3,4,5,6-tetrahydroxyxanthone (Structure 10):

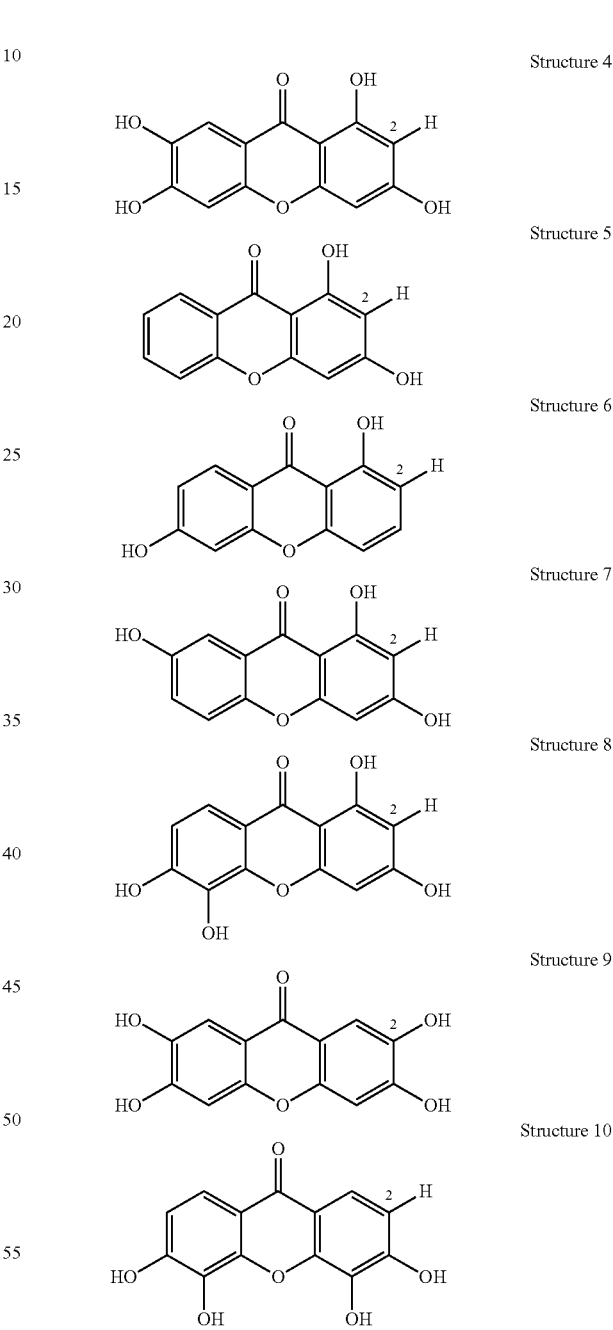

In these structures, the glycosyl group located at the C-2 position of Structure 1 is replaced by a hydrogen atom or a hydroxyl group.

In the polymer composition, the non-glycosylated xanthones can have similar anti-oxidant, anti-inflammatory, immunomodulatory and antiviral effects as the glycosylated xanthone, e.g., mangiferin.

The general structure of suitable hydroxylated xanthones can be represented by Structure 11:

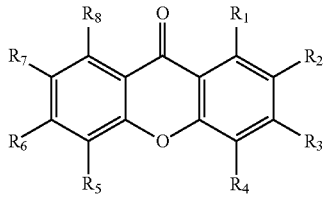

Structure 11 where $R_1$, $R_2$, $R_3$, $R_4$, $R_5$, $R_6$, $R_7$, and $R_8$ are independently selected from H, OH and glycosyl (structure 3), and at least one of $R_1$, $R_2$, $R_3$, $R_4$, $R_5$, $R_6$, $R_7$, and $R_8$ includes an OH.

The xanthone in the polymer composition may comprise a mixture of two or more xanthones.

The xanthone may constitute from 1-65% by weight of the polymer composition, e.g., at least 1% by weight, or at least 10% by weight. In one embodiment, it is present at up to 50% by weight of the polymer composition.

The xanthone may be miscible with the matrix material and/or dispersed in the matrix material. The resulting biocompatible polymer may thus be a solid polymer composition in which the xanthone is dispersed fairly homogeneously. In other embodiments, the xanthone may be concentrated at surfaces of the biocompatible polymer.

While the exemplary antioxidants disclosed herein are xanthones, other antioxidants and phytochemicals which are capable of being retained within a polymer matrix, e.g., by hydrogen bonding, and yet provide antioxidant or other beneficial properties to the polymer composition when brought into contact with a free-radical containing liquid, such as blood or other body fluid, are also contemplated.

The matrix material can be derived from one or more homopolymers or from monomers which react to form a polymer or copolymer. Exemplary homopolymers which may be used for the matrix material may be selected from the group consisting of polysulfones, polyamides, polyvinylpyrrolidones, polycarbonates, polycarbonates, polyacrylonitriles, and combinations thereof. "Polysulfones," as used herein, refers to a family of thermoplastic polymers which contain the subunit -aryl-$SO_2$-aryl-, more specifically -aryl-$SO_2$-aryl-O—, and includes a polymer of 4-[2-(4-hydroxyphenyl)propan2-yl]phenol and 4-(4-hydroxyphenyl)sulfonylphenol, commonly known as polysulfone, and a polymer of benzene-1,4-diol and 4-(4-hydroxyphenyl)sulfonylphenol commonly known as polyethersulfone. Polyethersulfone (PES) is also commonly known as polyarylethersulfone (PAES) and/or polyphenylsulfone (PPSU). Another suitable polysulfone is a copolymer of 4-(4-hydroxyphenyl)phenol and 4-(4-hydroxyphenyl)sulfonylphenol, also known as polyphenylsulfone. Other exemplary polysulfones are described in U.S. Pat. No. 5,911,880, the disclosure of which is incorporated herein by reference in its entirety. In one embodiment, the matrix material includes homopolymers of two or more of these polymers, e.g., a combination of a hydrophobic homopolymer(s) and a hydrophilic homopolymer(s). In one specific embodiment, the matrix material is predominantly formed from homopolymers selected from this group (i.e., at least 50%).

In another exemplary embodiment, the matrix material is formed from a blend comprising polyvinylpyrrolidone (PVP) and one or both of polyamide (PA) and polyethersulfone (PES) which may be substantially free of other homopolymers (i.e., less than 10 wt % of other homopolymers and in one embodiment, less than 5 wt % of other homopolymers). The polyethersulfone may constitute from 5-95% by weight of the PES/PVP blend, e.g., at least 40% by weight, or at least 50% by weight of the blend. In an embodiment, a PA/PES/PVP blend may be used to refine the final properties of the membranes and can be includes as part of the optimization process.

In the solid polymer composition, the homopolymers of the blend may be in the form of a block copolymer or are held together by weaker bonds, such as hydrogen bonds, or a combination thereof.

In an exemplary embodiment, the matrix material is formed from a blend of homopolymers, such as a blend of a polyamide and/or polyethersulfone and polyvinylpyrrolidone, as discussed above. The xanthone may comprise a hydroxylated xanthone, such as mangiferin. In one aspect, a biocompatible polymer composition may thus consist essentially of a polyamide and/or polyethersulfone, polyvinylpyrrolidone and at least one hydroxylated xanthone with other components accounting for no more than 10% by weight of the composition and in one embodiment, no more than 5% by weight. The at least one of a polyamide and a polyethersulfone may be present in the blend at least 5% by weight, e.g. at least 40% by weight, at least 50% by weight, up to 95% by weight.

FIG. 1 is a schematic diagram of a simplified hemodialysis circuit 10 including a dialyzer filter 20 including a container or housing 21 containing an exemplary semi-permeable membrane 22 formed from the exemplary biocompatible polymer composition. Blood from a patient 24 is removed through a venous blood line 26 with a blood pump 28 supporting circulating blood and through a heparin pump 30 towards the dialyzer filter 20. During dialysis, blood flows through the semi-permeable membrane 22 in one direction, with a dialysis solution flowing in the opposite direction. The dialysis solution is injected into the dialyzer filter 20 at a fresh dialysate port 32. Due to the difference in osmolarity between the two liquids, water traverses the membrane 22 in order to dilute the dialysis liquid, carrying along the impurities from the blood. The impurities are ejected through a used dialysate port 34. The dialysis fluid is used at body temperature, and may include a solution of glucose, amino acids and mineral ions. The cleansed blood is then returned to the patient 24 through a clean return blood line 36. Some or all of the components 26, 28, 30, 36 which come into contact with the blood may additionally or alternatively be formed from the exemplary biocompatible polymer composition and/or coated with a surface layer formed from the composition.

The semi-permeable membrane 22 may also be referred to as selectively-permeable membrane, a partially-permeable membrane or a differentially permeable membrane. It is a membrane that is permeable to water and may allow certain molecules or ions to pass through it by diffusion and occasionally specialized "facilitated diffusion." The rate of passage is dependent on pressure, concentration, and temperature of the molecules or solutes on either side, as well as the permeability of the membrane to each solute. Depending on the membrane and the solute, permeability may depend on solute size, solubility, properties and/or chemistry.

Figure 2:
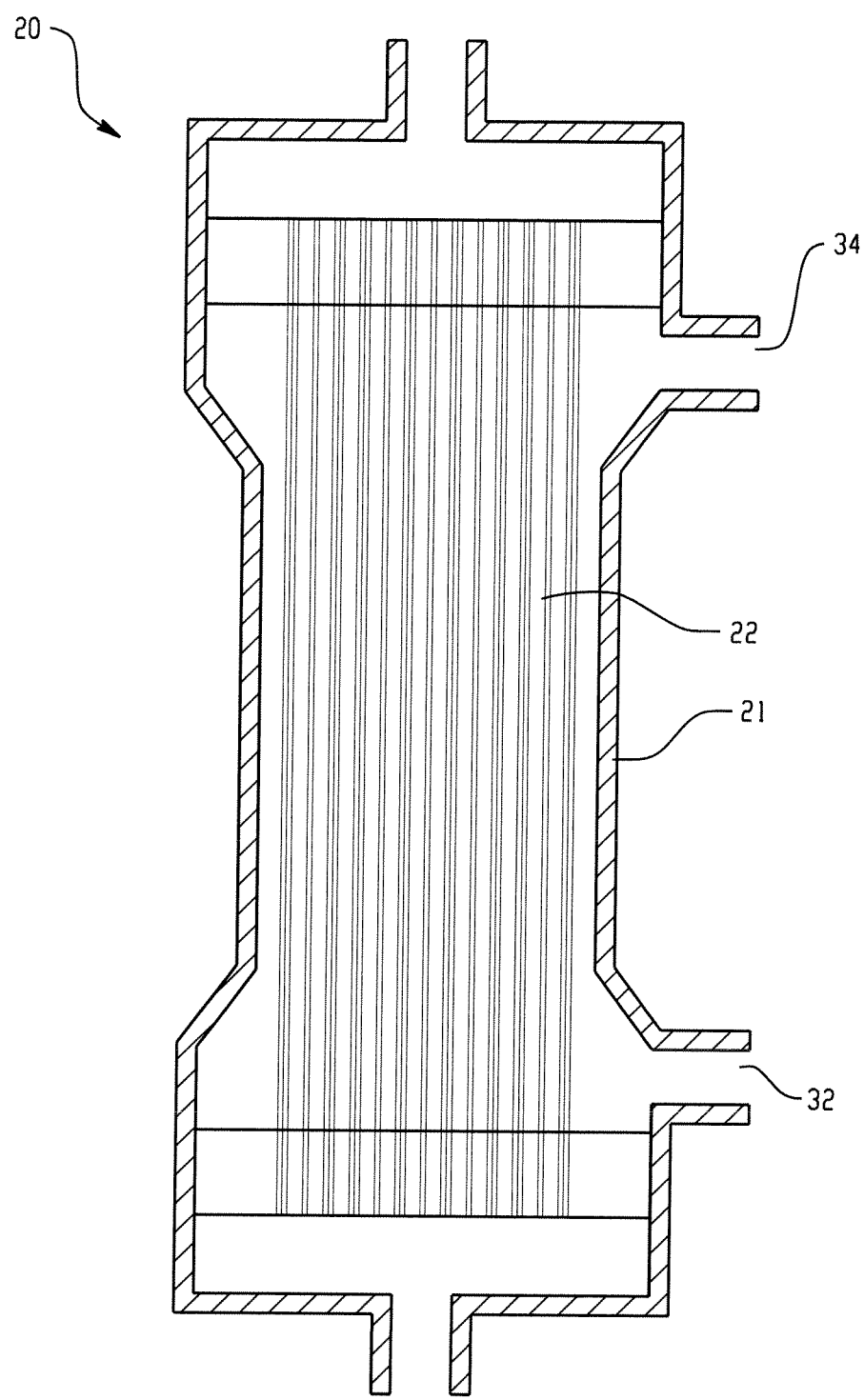
FIG. 2 is a schematic cross-sectional view of the dialyzer filter of FIG. 1.

FIG. 2 shows in a cross-sectional view of the dialyzer filter 20 containing the semi-permeable membrane 22. The membrane 22 may be formed substantially or exclusively from the biocompatible polymer composition. In other embodiments, the biocompatible polymer composition provides a surface layer or layers on a supporting structure, such as a hollow fiber.

The exemplary semi-permeable membrane 22, generally, provides some or all of the following: non-toxicity, biocompatibility, reduced complement activation and protein absorption, high filtration rates and physical stability. In the present exemplary embodiment, providing additional benefits such as anti-oxidant, anti-inflammation, anti-bacterial, anti-viral, anti-diabetic, and/or non-thrombogenic properties may give the hemodialysis filter the ability to reduce dialysis-induced-oxidative stress.

Additionally, an exemplary semi-permeable membrane with a non-thrombogenic property may allow for elimination of heparin pump 30 from the circuit as administering heparin may no longer be needed. Heparin is used as an anti-coagulant in the blood acting to prevent blood clots from forming. A serious side effect from heparin, however, may be heparin-induced thrombocytopenia. This along with dialysis-induced-oxidative stress may be reduced using the semi-permeable membrane 22 within the hemodialysis system 10.

The semi-permeable membrane 22 may be in the form of a thin film or an arrangement of fibers, such as a bundle of hollow fibers. In other embodiments, the membrane is in the form of a porous sponge or other porous structure which allows blood to pass therethrough.

Figure 3:
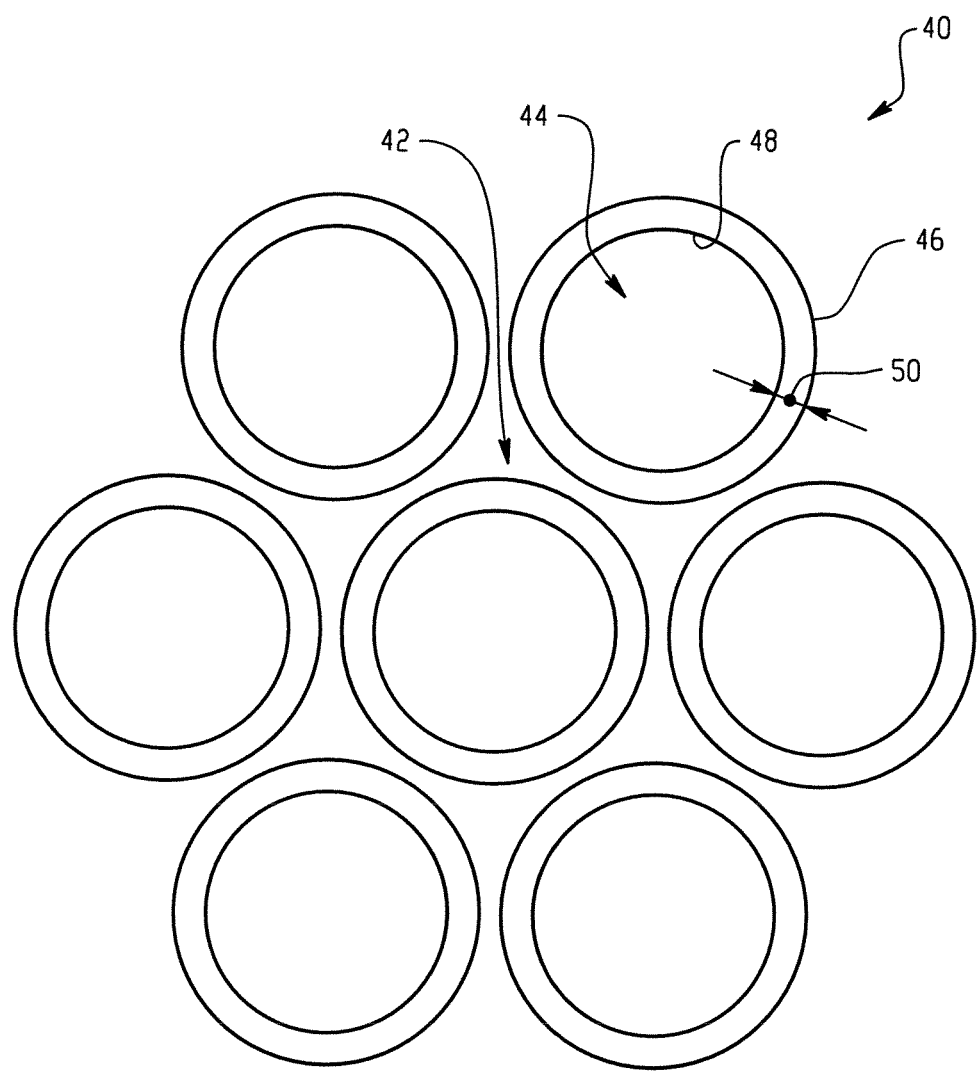
FIG. 3 is a schematic of a cross-sectional view of an array of hollow fibers within an exemplary semi-permeable membrane formed from the biocompatible polymer composition.

FIG. 3 is a cross-sectional view of an exemplary membrane 22 comprising an array of hollow fibers 40. The fibers may be arranged generally in parallel, with spaces 42 between the fibers. Hollow fiber 40 may have a continuous hollow cavity 44, an outer wall surface 46 which forms an outer side of the fiber, and an inner wall surface 48 which defines the limits of the continuous hollow cavity 44. A wall thickness 50, measured between the outer wall surface 46 and the inner wall surface 48 of the hollow fiber 40, may be less than 100 µm, e.g., from 5-50 µm, such as from 5-35 µm. The cross-sectional diameter of the fibers may be less than 200 µm, e.g., from 10-100 µm, such as from 20-70 µm.

The exemplary dialyzer filter 20 can be formed by forming a semi-membrane 22 from the polymer composition, and inserting the semi-membrane 22 into the dialyzer filter housing 21.

The filter 20 can be used for filtering any blood or any other free-radical containing fluid. In one embodiment, a method of removing free radicals from a fluid includes filtering a fluid with the semi-permeable membrane 22 described above, whereby free radicals in the fluid pass through by the semi-permeable membrane 22 and are removed from the fluid.

While the biocompatible polymer composition has been described in terms of a hemodialysis filter which can be used for hemodialysis and/or hemofiltration, it is also contemplated that it may be used in the forming of other medical devices, including medical tubing, such as a vascular implant, a vascular graft, stent, stent graft, or catheter for insertion into the vascular system of a living being. The medical device may include, in at least a surface layer thereof, at least one antioxidant, such as a hydroxylated xanthone, as described above, at a concentration of at least 0.1 wt %, and which may further include a polymer matrix as described above.

Forming the Biocompatible Polymer Composition and Membrane

A solution blending process can be used to form the biocompatible polymer composition. Solutions of neat (or undiluted) PA, PVP, mangiferin and their blends can be prepared in dimethylsulfoxide at a polymer concentration of 10 wt % in a reaction vessel. Solvents, such as dimethylacetamide, or dimethylformamide, may also be used in the preparation process. The liquid mixture was stirred or homogenized at a suitable temperature (e.g., room temperature) for sufficient time for the components to mix thoroughly (e.g., for at least 48 hours) to form a PA/PVP/mangiferin/dimethylsulfoxide liquid blend. Room temperature can be considered to be from about 20° C. (68° F.) to 28° C. (82.4° F.). This can be followed by solvent casting under vacuum at 150° C. for 24 hours or other methods to remove solvent or reduce solvent concentration. It may be appreciated that the solution blending process can similarly be used to form a PES/PVP/mangiferin/dimethylsulfoxide liquid blend.

In another embodiment, a melt blending process can be used to form the biocompatible polymer composition. A suitable composition ratio of polyamide and polyvinylpyrrolidone is combined in a reaction vessel and heated to above their glass transition temperatures ($T_g$) which ranges from 140° to 160° C., but below their decomposition temperatures, for up to 20 minutes. For example, the mixture of homopolymers may be heated up to about 250° C. When the mixture is viscous or exhibits a high resistance to flow, an amount of xanthone, e.g., mangiferin, is added and mixed for up to 5 minutes. In some embodiments, a small amount of solvent, such as dimethylsulfoxide, may be added to the mixture to provide better homogenization. The solvent may be later removed. It may be appreciated that the melt blending process can be used to form a PES/PVP/mangiferin/dimethylsulfoxide liquid blend.

The polyamide, polyethersulfone, and polyvinylpyrrolidone used for forming biocompatible polymer compositions may be homopolymers. Prior to mixing, the homopolymers may each have a weight average molecular weight ($M_w$) from 1,000 to 3 million grams/mole, e.g., at least 10,000 grams/mole, such as at least 20,000 grams/mole or at least 30,000 grams/mole. In one embodiment, $M_w$ for each homopolymer is less than 200,000 grams/mole, e.g. less than 100,000 grams/mole.

The polyamide and polyethersulfone used for forming the blends may be amorphous or semi-crystalline polymers. In amorphous polymers, the membrane formation is not complicated by the matrix crystallization. Typically, aliphatic polymers may tend to be crystalline as the monomer units can pack inside a crystalline lattice. However, the addition of aromatic units may disrupt the crystalline packing. At high aromatic contents the system tends to be amorphous. Aliphatic/aromatic refers to the chemical composition of the monomers that constitute the polymer. Amorphous refers to the physical property wherein the polymer is not able to crystallize. Exemplary polyamides include amorphous polyamides having a glass transition temperature $T_g$ of at least about 140° C. Exemplary polyethersulfones include amorphous polyethersulfones having a glass transition temperature $T_g$ of at least about 230° C. Other forms, such as aliphatic and aromatic polyamides and polyethersulfones, may require strong acids such as sulfuric, hydrochloric, methane sulfonic acid and formic acid to be used to form the initial solution.

Exemplary polyamides include nylon, such as, nylon-6, nylon-6,3, nylon-6,6, nylon-6/3T, and combinations, thereof.

Exemplary polyethersulfones include those sold by BASF under the trade name of ULTRASON® E, such as ULTRASON® E 6020P.

In the PA/PVP and PES/PVP blends, the polyvinylpyrrolidone homopolymer imparts hydrophilicity and the amorphous polyamide and polyethersulfone homopolymers impart hydrophobicity. The amorphous polyamide and polyethersulfone homopolymers additionally exhibit viscoelastic properties to form good films and fibers. The viscoelasticity allows the composition to undergo deformation when a stress is applied.

In an exemplary embodiment, the method of forming the biocompatible polymer composition includes combining the matrix material and at least one xanthone in the presence of a solvent, thereby forming a matrix material/xanthone/solvent blend. The solvent can be at least one of dimethylsulfoxide, dimethylacetamide, and dimethyl formamide. The matrix material/xanthone/solvent blend is a liquid.

The matrix material and xanthone may together constitute from 1-25% by weight of the matrix material/xanthone/solvent blend, e.g., at least 5% by weight, or at least 10% by weight of the blend. The PA:PVP and PES:PVP ratios in the blends may be from 1:99 to 99:1, e.g., from 10:90 to 90:10, and in one embodiment from 40:60 to 70:30, e.g., greater than 50:50. The xanthone:matrix material ratio in the liquid blend may be from 1:99 to 99:1, e.g., less than 50:50.

The polymer composition can be isolated by immersion of the PA/PVP/mangiferin/solvent and PES/PVP/mangiferin/solvent blends respectively into a non-solvent, such as water. The non-solvent displaces the solvent in the blends inducing phase separations of PA/PVP/mangiferin/dimethylsulfoxide/water and PES/PVP/mangiferin/dimethylsulfoxide/water blends. A phase (phase I) may include a blend having higher polyamide and polyethersulfone concentrations within the matrix material. Another phase (phase II) may include a blend having lower polyamide and polyethersulfone concentrations within the matrix material. An exemplary embodiment shown to exhibit good mechanical properties may be a blend having higher polyamide and polyethersulfone concentrations within the matrix material. Therefore, phase I may be used to form a membrane while Phase II is discarded. In other embodiments, the solvent may be removed through evaporation.

Increased protein resistance and decrease complement activation may be produced through optimizing the hydrophobic/hydrophilic domains of PA/PVP respectively and PES/PVP respectively by adjusting blend ratios. This can be advantageous from a bio-compatibility standpoint.

Fibers 40 for the semi-permeable membrane 22 may be fabricated from the polymer composition (which may be in the form of a solvent-containing liquid blend or solvent-free) according to a variety of methods known in the art including electrospinning, gas jet (NGJ), wet spinning, dry spinning, melt spinning, and gel spinning. Some of these methods start with a solution of a fiber-forming polymer dispersed in a suitable solvent. In the electrospinning method, for example, an electrical potential is applied between a droplet of the solution and a collector positioned below it. The droplet extends rapidly under the applied potential. The solvent evaporates from the solution, forming fibers before they reach the collector. Electrospinning tends to produce very thin (i.e. fine denier) fibers. Typically, electrospun fibers have very small diameters, usually on the order of about 3 nanometers to about 3000 nanometers.

A suitable method for producing hollow fibers is known as the fibers by gas jet (NGJ) method. In this method, a device having an inner tube and a coaxial outer tube with a sidearm is provided. The inner tube is recessed from the edge of the outer tube, thus creating a thin film-forming region. Polymer melt is fed in through the sidearm and fills the empty space between the inner tube and the outer tube. The polymer melt is prepared by the melt blend process as described above. The polymer melt continues to flow toward the effluent end of the inner tube until it contacts the effluent gas jet at the edge of the inner tube where it opens into the outer tube. The gas jet impinging on the melt creates a thin film of polymer melt in the region between the edges of the inner and outer tubes, which travels to the effluent end of the outer tube where it is ejected forming a turbulent cloud of hollow fibers. In the present embodiment, the polymer melt comprises the matrix material and a xanthone.

In another exemplary embodiment, the fibers 40 are formed by solution spinning. These fibers can be produced from a solution of the two homopolymers, a xanthone, and a solvent, such as dimethylsulfoxide, by spinning the solution through an appropriately constructed shaping annular die of a hollow-needle nozzle into a precipitation liquid. An example of a precipitation liquid which may be used is water. The production conditions can be tailored in such a way that an external skin or an internal skin or both are formed. The wall thickness of hollow fibers 40 of this type is usually in the range from about 5 to 500 μm.

To form the membrane, the fibers 40 can be held together as a bundle, e.g., by sealing the edges of the fiber bundle using an epoxy.

Other methods for forming fibers 40 and semi-permeable membranes 22, which may be used herein, are disclosed, for example, in U.S. Pat. Nos. 4,935,141, 5,505,851, 5,152,894, 6,382,526 and 6,520,425, and U.S. Pub. No. 2007/0207179, the disclosures of which are incorporated herein by reference.

Without intending to limit the scope of the exemplary embodiment, the following examples demonstrate properties of the composition.

EXAMPLES

Materials

An amorphous polyamide nylon-6/3T (TROGAMID® T5000) ($M_n$=20,000 and $M_w$=63,000) (Degussa Corporation, Germany) having a water absorption of 5.1 wt % was used as the polyamide. An amorphous polyethersulfone (ULTRASON® E 6020P) (Mw=46,000 and $T_g$=230° C.) (BASF Corporation) approved by the FDA and commonly employed in dialyzer membrane applications was used as the polyethersulfone. Polyvinylpyrrolidone ($M_w$=40,000 g/mol) (Sigma Aldrich, USA) was also used. Dimethylsulfoxide, dimethylacetamide, and dimethylformamide (Sigma-Aldrich, USA) were used as solvents. Mangiferin ($M_w$=422.3 g/mol) was obtained from (Sigma Aldrich, USA). All materials were reagent grades and used without further purification.

Preparation of a Polyamide/Polyvinylpyrrolidone/Mangiferin/Solvent Blend

Various composition ratios of PA/PVP/mangiferin blends were prepared and dissolved in dimethylsulfoxide (DMSO) with the blend being about 10% by weight concentration in the mixture with DMSO. The composition ratios (% by weight) for the PA/PVP blends prepared were 0/100 (Pure PVP), 25/75 (PA/PVP), 50/50 (PA/PVP), 75/25 (PA/PVP), and 100/0 (Pure PA). Mangiferin varied from 0% up to 50% by weight of the PA/PVP/mangiferin blend and the PES/PVP/mangiferin blend respectively. PES/PVP/mangiferin blends were similarly prepared.

Membrane Casting

In one test, thin films of the PA/PVP/mangiferin/DMSO and PES/PVP/mangiferin/DMSO blends of various ratios were prepared by depositing the blends on a microscopic slide and vacuum-drying at 190° C. to evaporate the dimethylsulfoxide solvent. The residues remaining on the glass sides were analyzed by an optical microscope to determine various phases existing in the compositions. Ternary phase diagrams were mapped identifying regions representing the different phases.

In another test, PA/PVP blend copolymers and PES/PVP blend copolymers were prepared by vacuum-drying the copolymers at 80° C. for 24 hours and subsequently dissolving in the various solvents, such as dimethylsulfoxide, dimethylacetamide, and dimethylformamide, at various PA/PVP and PES/PVP ratios. The solutions were mixed thoroughly for 48 hours and degassed under vacuum at room temperature. Membranes were then prepared by spreading the homogenized solutions in the form of a film on a pre-cleaned glass plate followed by immersion into non-solvent (Reverse Osmosis grade water unless otherwise mentioned) maintained at 25° C. The coagulated membranes were then peeled off the glass plate, rinsed with excess water and dried at 50° C. for analysis, such as morphology analysis. This same membrane casting method can be used for blends of PA/PVP copolymers and PES/PVP copolymers with an amount of mangiferin.

These methods were used for ease of analysis of the composition and are not intended to be representative of optimal methods for forming membranes.

Figure 4:
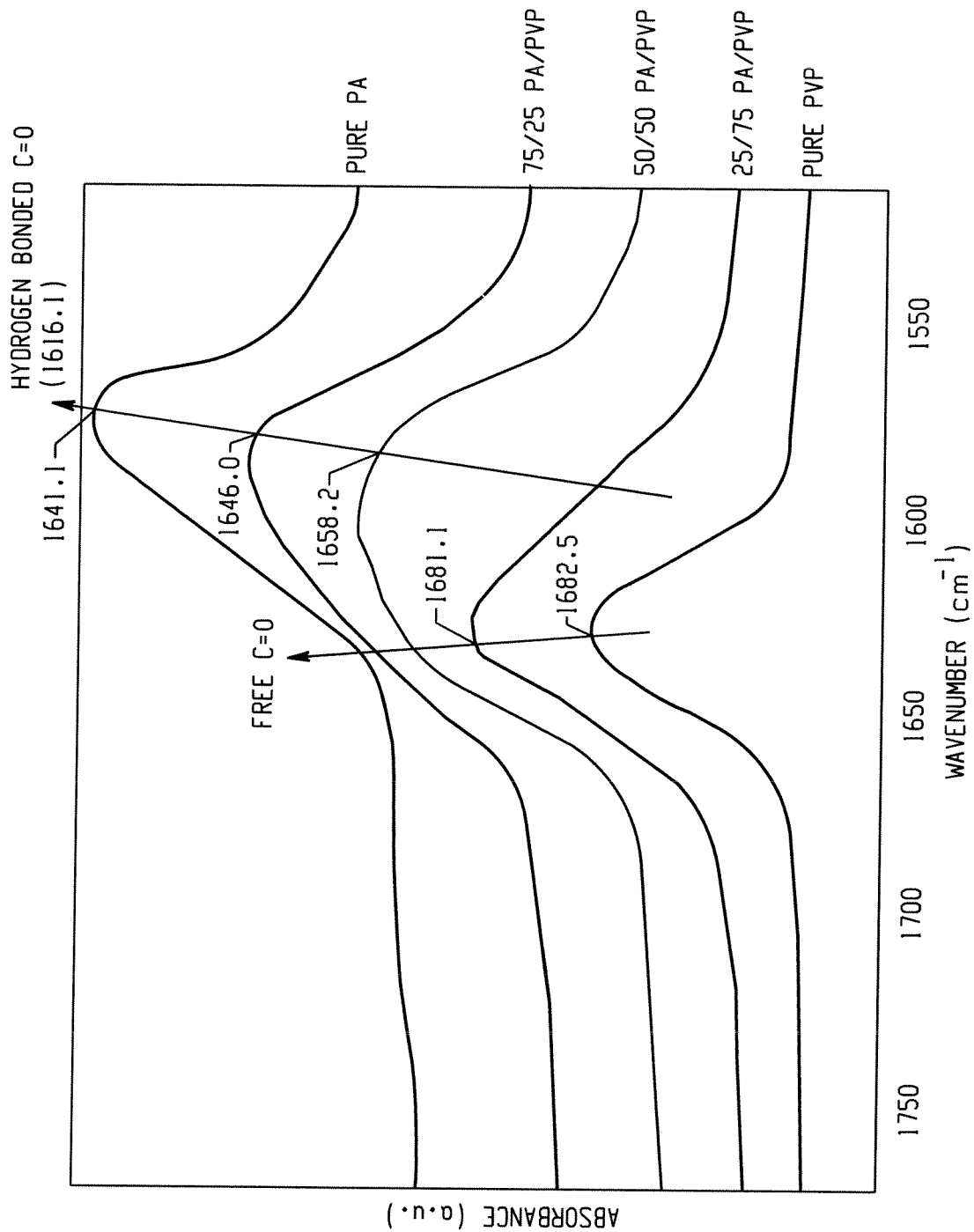
FIG. 4 shows Fourier transform infrared (FTIR) spectra for polyamide (PA)/polyvinylpyrrolidone (PVP) combinations as a function of blend ratio with the range of about 1500-1750 $cm^{-1}$.
Figure 5:
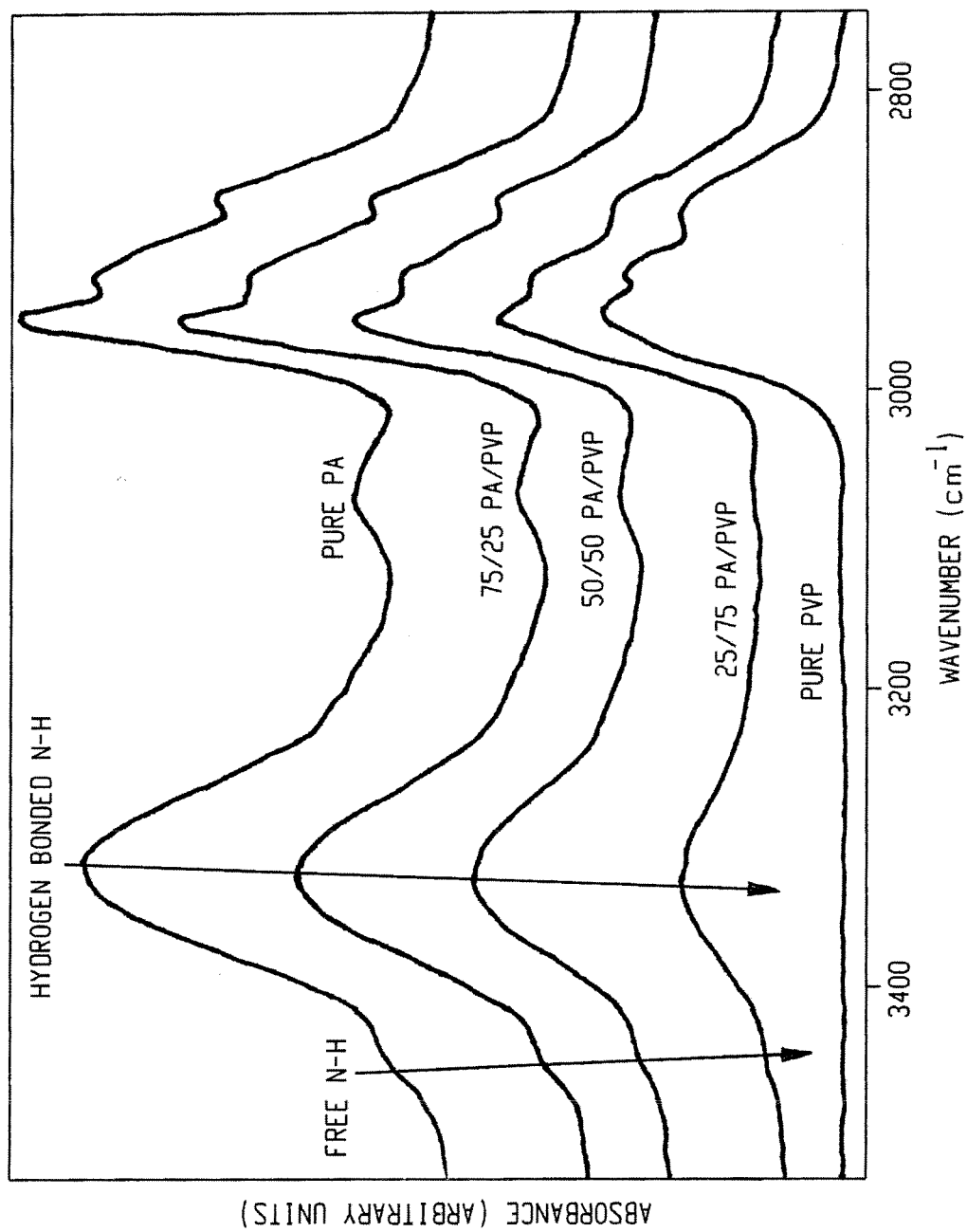
FIG. 5 shows FTIR spectra for polyamide/polyvinylpyrrolidone combinations as a function of blend ratio in the range of about 2800-3500 $cm^{-1}$.
Figure 6:
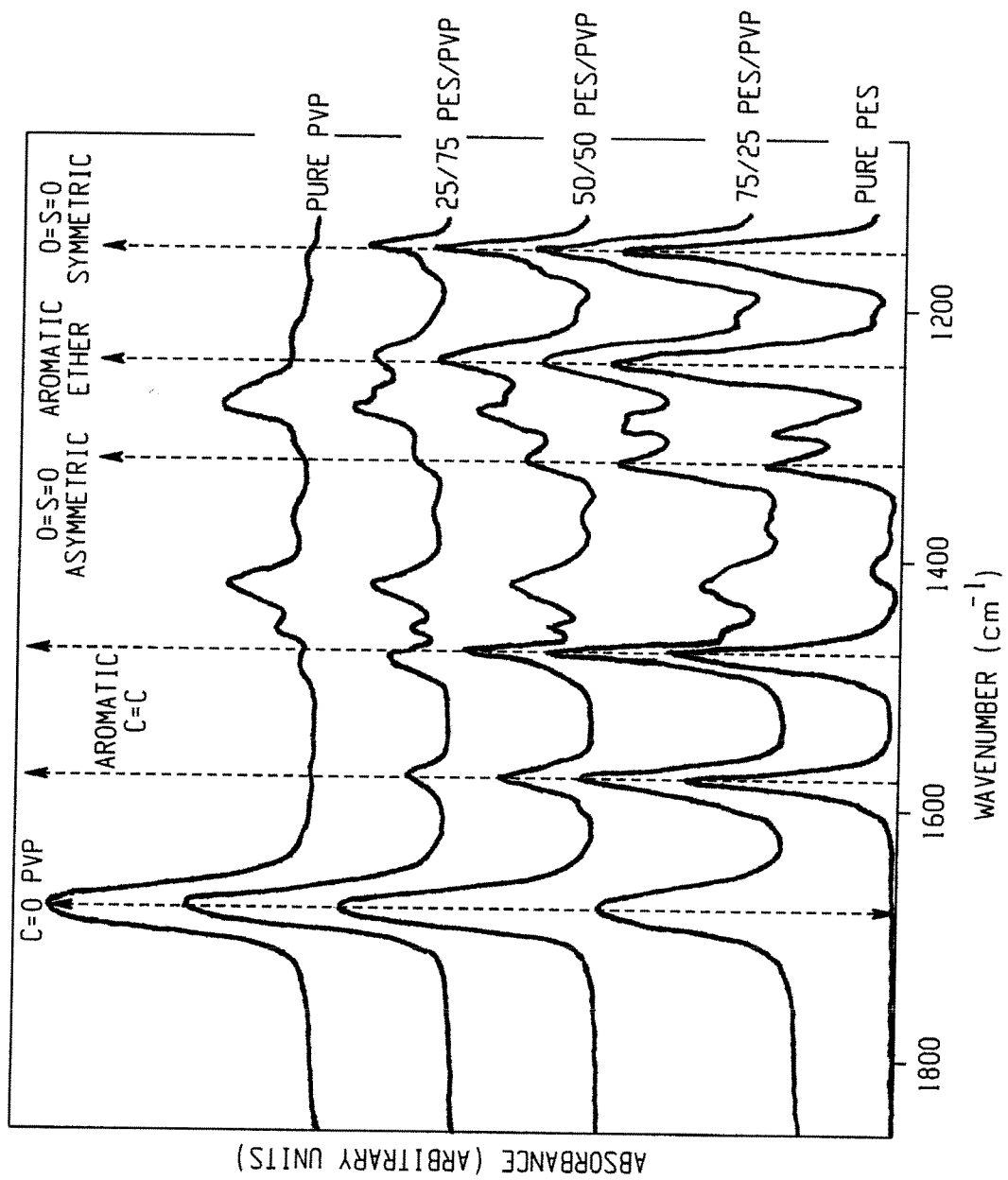
FIG. 6 shows FTIR spectra polyethersulfone (PES)/polyvinylpyrrolidone combinations as a function of blend ratio in the range of about 1300-1800 $cm^{-1}$.
Figure 7:
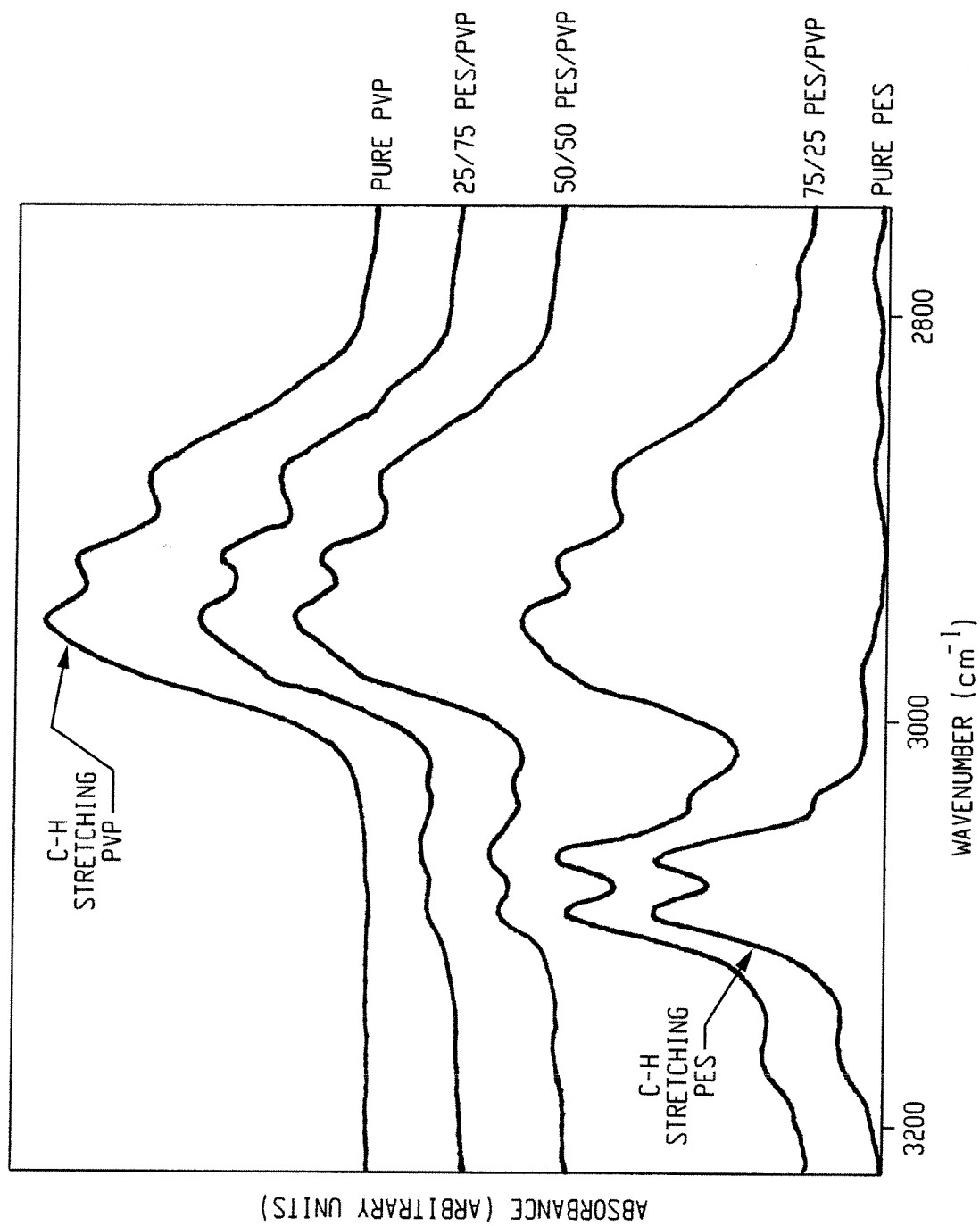
FIG. 7 shows FTIR spectra for polyethersulfone/polyvinylpyrrolidone combinations as a function of blend ratio in the range of about 2800-3500 $cm^{-1}$.

FIGS. 4-10 illustrate the effects on the carbonyl frequency of the carbonyl group in PA, PES, and PVP when combined with one another and mangiferin. In an exemplary embodiment, hydrogen bonding occurs between the various components, e.g., PA/PVP, PES/PVP, PA/mangiferin, PES/mangiferin, and PVP/mangiferin. FTIR spectra were obtained at 100° C. Infared spectroscopy exploits the fact that PA, PES, and PVP have specific frequencies at which they rotate or vibrate corresponding to discrete energy levels (vibrational modes). By measuring at a specific frequency over time, changes in the character or quantity of a particular bond can be measured. FIGS. 4, 5, and 8-10 illustrate hydrogen bonding between the carbonyl of PVP and the amide nitrogen of PA, the carbonyl of PA and the hydroxyl of mangiferin, the aromatic ether of PES and the hydroxyl of mangiferin, and the carbonyl of PVP and the hydroxyl of mangiferin, respectively, where there is a shift of the carbonyl peaks of PVP, PA, and PES to a lower frequency. FIGS. 6 and 7 illustrate that no hydrogen bonding occurs between the aromatic ether of PES and the carbonyl of PVP. However, PVP is a tertiary amide which is highly electronegative in nature. The electrostatic dipolar interaction between the sulfone of PES and the tertiary amide group of PVP may lead to the miscibility of their blends.

FIGS. 4 and 5, show FTIR spectra of the PA/PVP blends in the ranges 1550-1800 $cm^{-1}$ and 2750-3550 $cm^{-1}$. FIG. 4 illustrates cross-hydrogen bonding by the systematic movement of free carbonyl (C=O) peak to lower wavenumbers (shifted by approximately 8 $cm^{-1}$) and freeing up of hydrogen-bonded carbonyl groups (C=O) shifting to higher wavenumbers (shifted by approximately 17 $cm^{-1}$). FIG. 5 illustrates the release of some of the self-associated N—H groups of PA which causes the 3322 $cm^{-1}$ band to shift to a higher wavenumber (shifted by approximately 10 $cm^{-1}$) and formation of cross-hydrogen bonding of the free N—H of PA showing a blue shift (approximately 15 $cm^{-1}$) upon addition of PVP.

FIGS. 6 and 7 show FTIR spectra of the PES/PVP blends in the regions of 1550-1800 $cm^{-1}$ and 2750-3550 $cm^{-1}$, respectively. In the 2750-3550 $cm^{-1}$ region, there was little of no movement of any characteristic band (i.e., 2 $cm^{-1}$ for ether band, 1 $cm^{-1}$ for C=O mangiferin, 1 and 2 $cm^{-1}$ for symmetric and asymmetric O=S=O bands, respectively) suggesting no indication of strong specific interactions between the PES/PVP pair.

Figure 8:
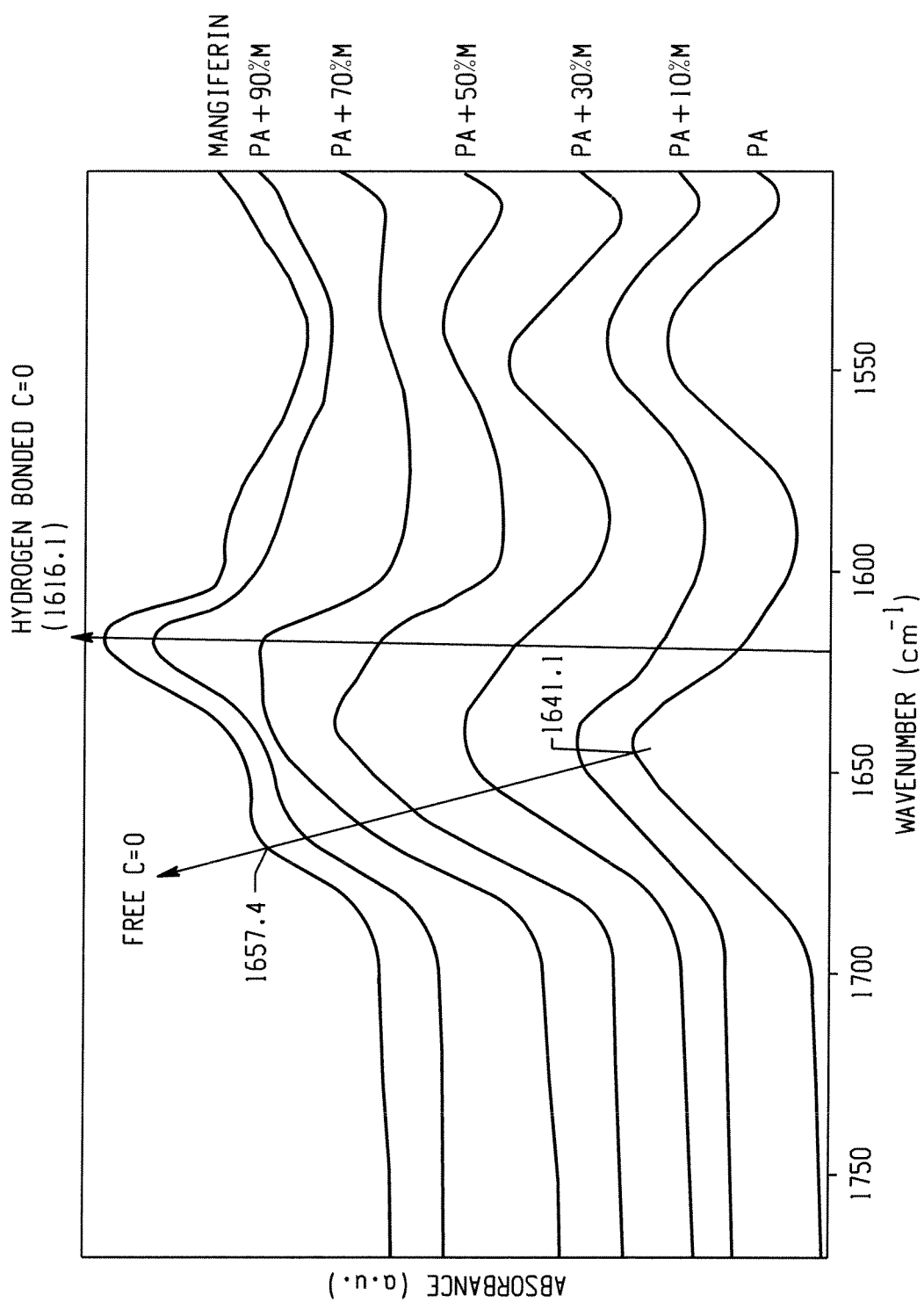
FIG. 8 shows FTIR spectra polyamide/mangiferin (M) combinations as a function of blend ratio in the range of about 1500-1750 $cm^{-1}$.

FIG. 8 shows FTIR spectrum of PA/mangiferin blends in the 1500-1800 $cm^{-1}$ range. As is known in the art, PA molecules can self-associate and form self-hydrogen bonding within their own species. Both PA and mangiferin can self-associate among themselves via self-hydrogen bonding (i.e., intermolecular hydrogen bonding among the same species). With the addition of mangiferin, the amide-I band of PA exhibits a spectral shift (approximately 8 $cm^{-1}$) to lower wavenumbers due to hydrogen bonding with hydroxyl groups of mangiferin. The C=O band of mangiferin shows a marginal shift to a lower wavenumber of about 4 $cm^{-1}$. This may suggest a possibility of N—H—C=O interaction. In contrast, the aromatic C=C band does not show any movement suggesting that since it may not be involved in any specific interaction.

Figure 9:
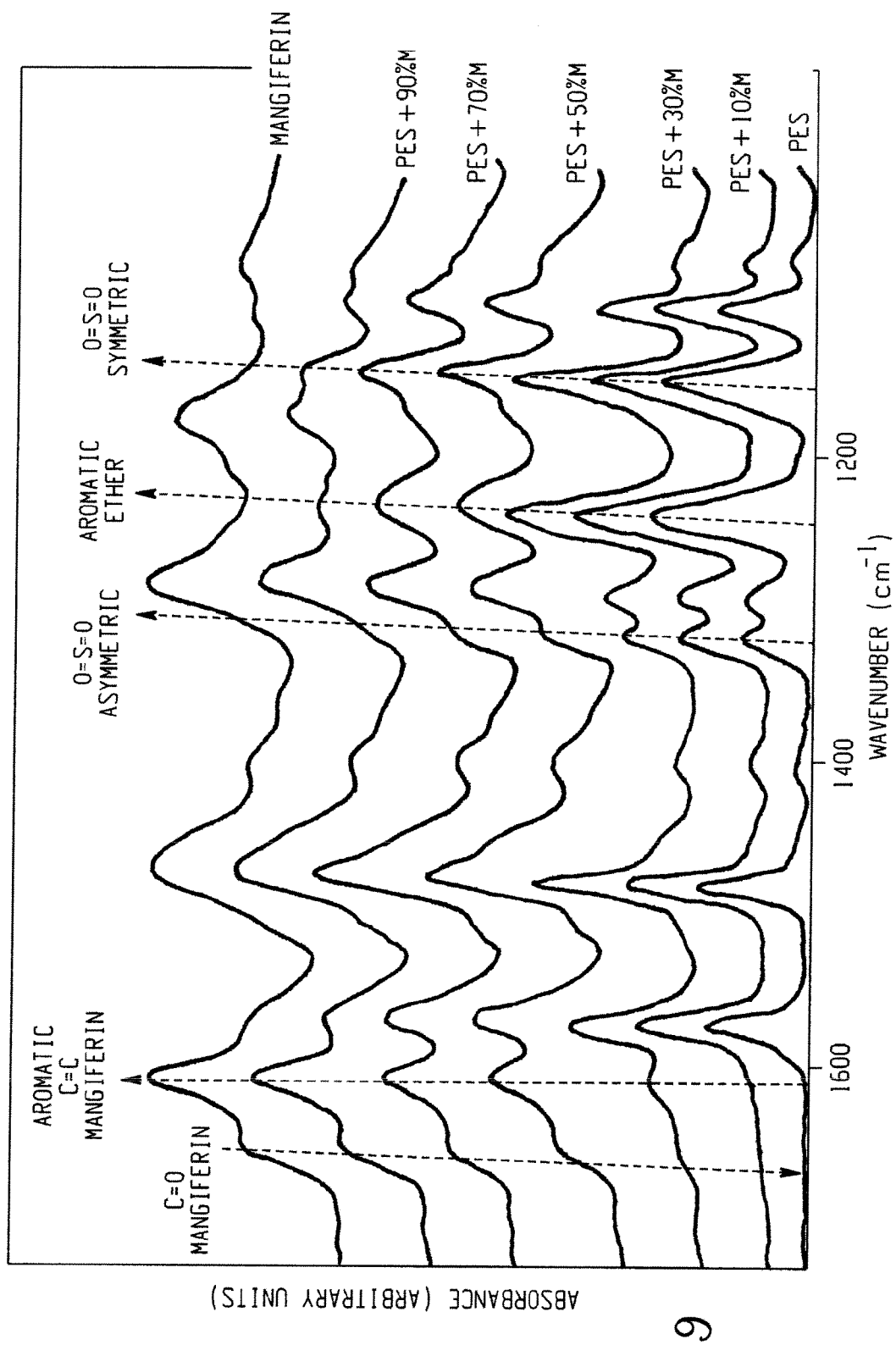
FIG. 9 shows FTIR spectra for polyethersulfone/mangiferin combinations as a function of blend ratio in a range of about 1000-1650 $cm^{-1}$.

FIG. 9 shows FTIR spectra of PES/mangiferin blends in the 1500-1800-$cm^{-1}$ range. Both PES and mangiferin can self-associate among themselves via self-hydrogen bonding (i.e., intermolecular hydrogen bonding among the same species), while PES, although unable to self-associate, may be capable of interacting with mangiferin (i.e., cross-hydrogen-bonding). With the addition of mangiferin, it is shown that the asymmetric and symmetric stretching bands of O=S=O shift 4 and 6-$cm^{-1}$, respectively, and the aromatic ether of PES shifts to lower frequencies by 6 $cm^{-1}$ due to cross-hydrogen bonding with the hydroxyl groups of mangiferin. Therefore, some of the self-hydrogen bonded groups in mangiferin may be released, resulting in a red shift of the carbonyl band of mangiferin of 8 $cm^{-1}$ at 1658 $cm^{-1}$. The aromatic C=C band, in contrast, does not show any movement because the C=C stretching is not directly involved in any specific interactions.

Figure 10:
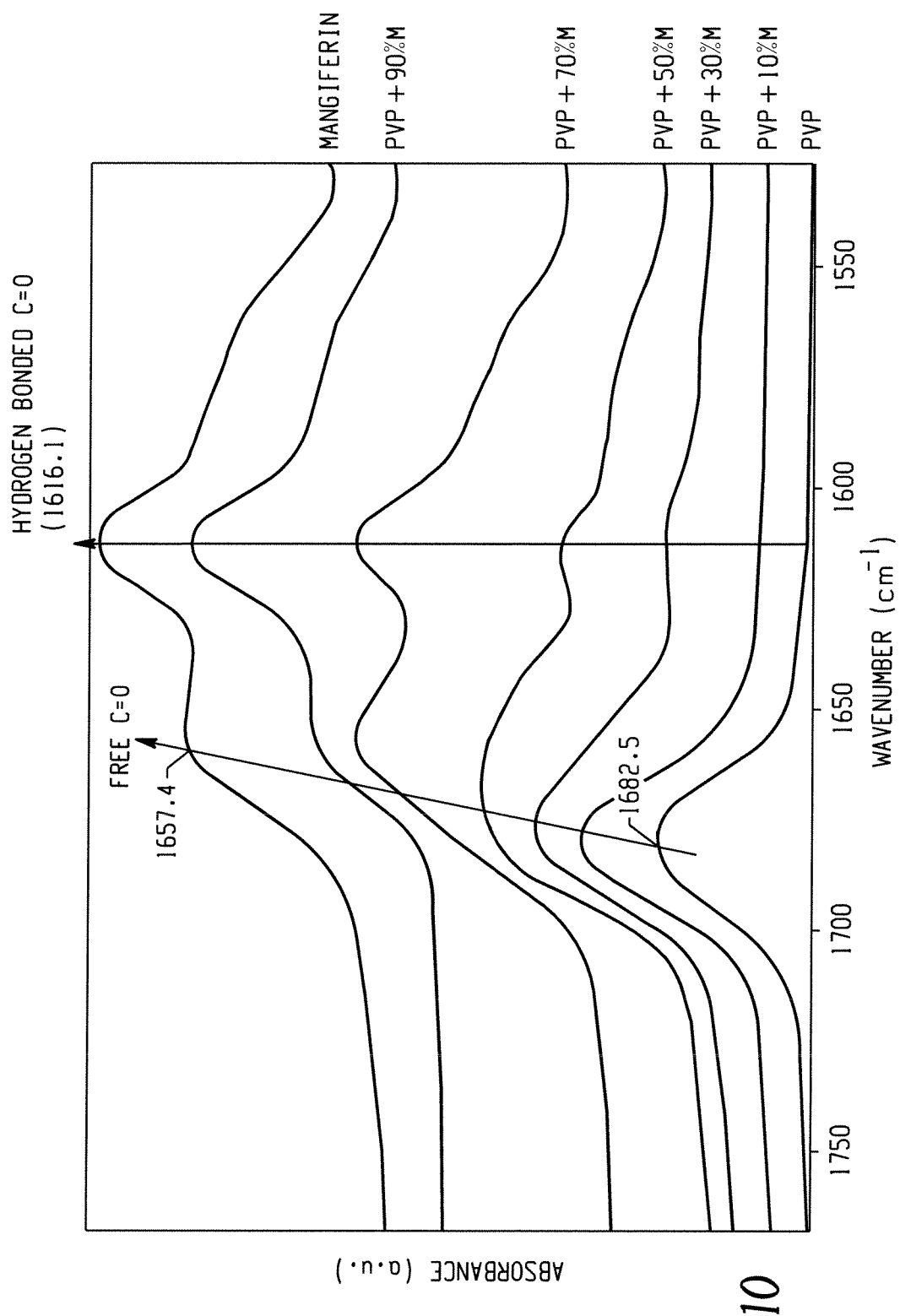
FIG. 10 shows FTIR spectra for polyvinylpyrrolidone/mangiferin combinations as a function of blend ratio in a range of about 1550-1750 $cm^{-1}$.

FIG. 10 shows FTIR spectra of PVP/mangiferin blends in the 1500-1800 $cm^{-1}$ range. FIG. 10 illustrates systematic movement of carbonyl bands of both PVP and mangiferin constituents (approximately 25 $cm^{-1}$) in contrast to the stationary aromatic C=C band of mangiferin showing no spectral shift.

Ternary Phase Diagram Analyses

Figure 11:
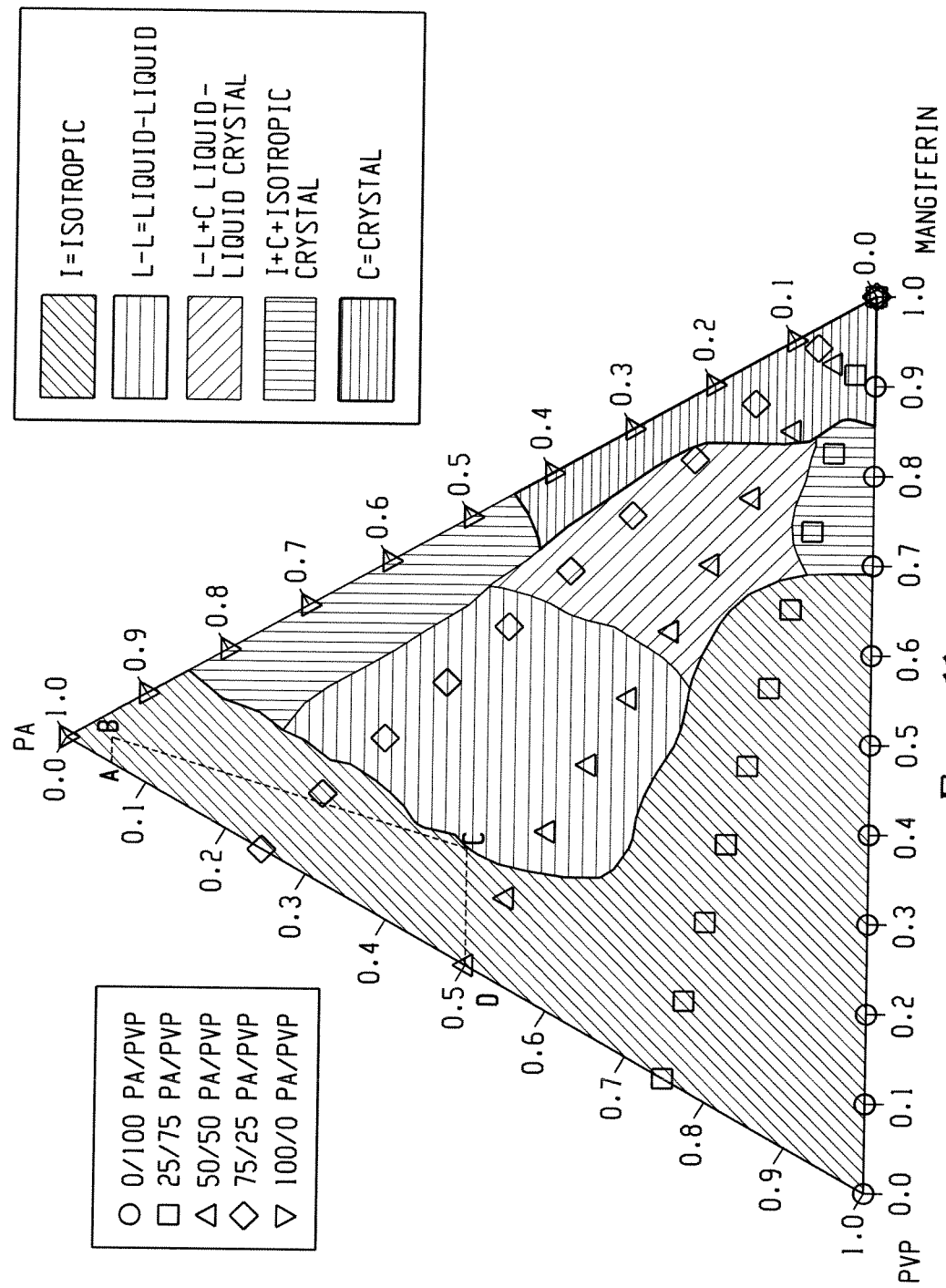
FIG. 11 is a ternary phase diagram for polyamide/polyvinylpyrrolidone/mangiferin as a function of blend ratio.
Figure 12:
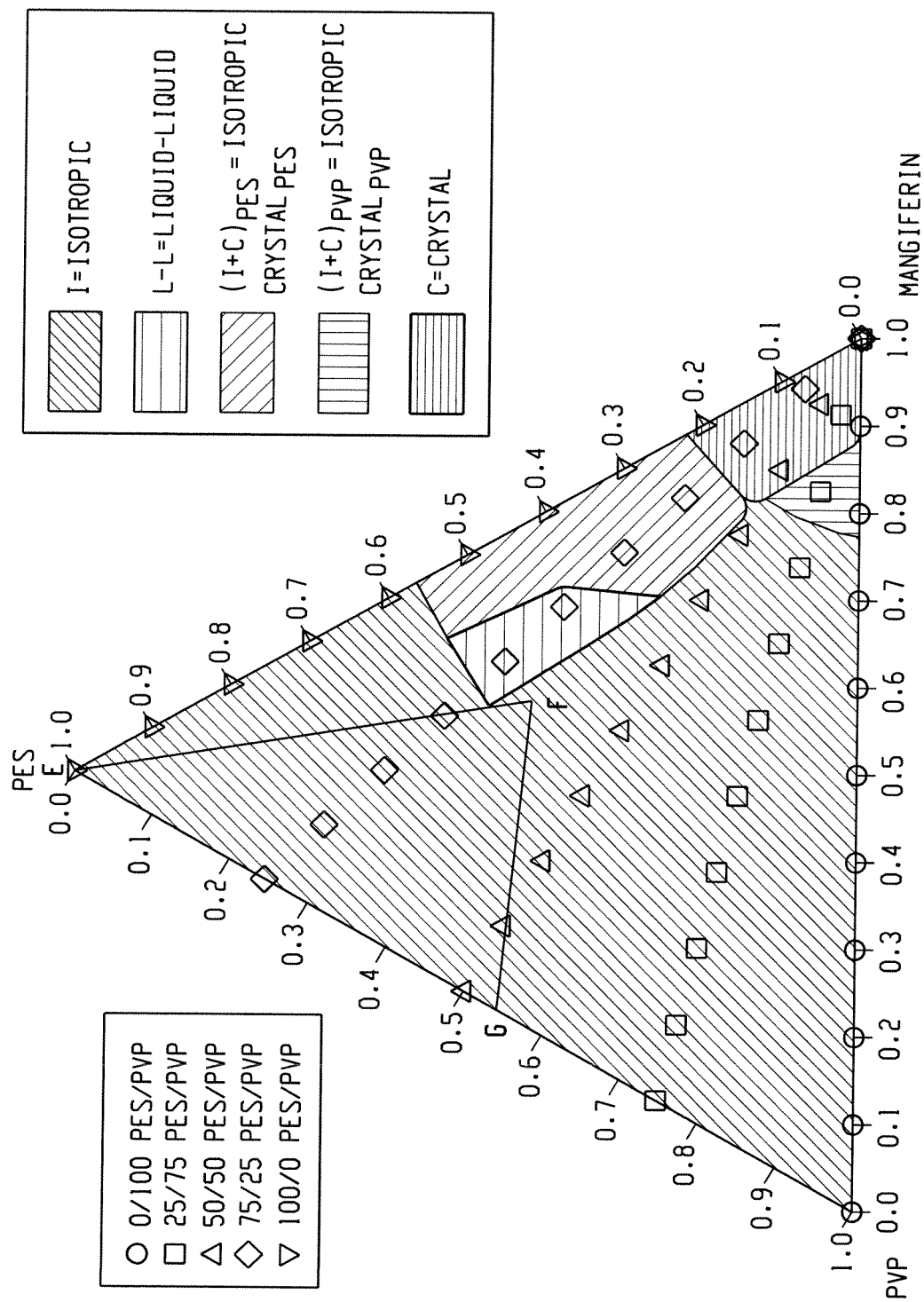
FIG. 12 is a ternary phase diagram for polyethersulfone/polyvinylpyrrolidone/mangiferin as a function of blend ratio.

FIGS. 11 and 12 are a ternary phase diagrams between the three components mangiferin, polyamide, and PVP, with various phases present and mangiferin, polyethersulfone, and PVP, with various phases present. The diagrams show that there are isotropic, liquid-liquid, liquid-liquid plus crystal, isotropic plus crystal and crystal phase separation regions, depending on the concentration ratios. The isotropic phase indicates that the composition has the same properties in all directions. The liquid-liquid phase is a phase separated structure in which one phase contains PA with some dissolved quantity of mangiferin and the other phase contains PVP with some dissolved quantity of mangiferin. The fluids can freely form a distinct surface at the boundaries of its bulk material. The crystal phase is a solid in which the constituent atoms, molecules or ions are packed in a regularly ordered, repeating pattern extending in all three spatial dimensions.

FIG. 11 illustrates that blends with high polyamide and polyvinylpyrrolidone concentrations such as 100/0 (PA/PVP) and 0/100 (PA/PVP) form an isotropic phase. Blends with high mangiferin concentrations, such as greater than 70% by weight, form a crystalline phase. Intermediate compositions of PA/PVP with lower concentrations of mangiferin form liquid-liquid phase separations. Liquid-liquid phase separation plus a crystal phase forms with increasing concentrations of mangiferin. The area outlined by A-B-C-D of FIG. 11 further illustrates exemplary embodiments exhibiting both isotropic and liquid-liquid phases which may be used for forming the exemplary membrane.

FIG. 12 illustrates that blends with high polyethersulfone and polyvinylpyrrolidone concentrations, such as Pure PES and Pure PVP, form an isotropic phase. Blends with high mangiferin concentrations, such as greater than 78% by weight, form a crystalline phase. Intermediate compositions of PES/PVP with lower concentrations of mangiferin form liquid-liquid phase separations. Increasing concentrations of mangiferin form a isotropic plus crystal phase. The area outlined by E-F-G of FIG. 12 further illustrates exemplary embodiments exhibiting an isotropic phase which may be used for forming the exemplary membrane.

Compared with a PA/PVP/mangiferin system, the PES/PVP/mangiferin system exhibits a large single phase region with smaller liquid plus liquid and solid plus liquid coexistence regions. This may provide useful guidance to controlling the membrane formation step. That is, a wide range of ternary composition can be available in order to prepare an initially homogeneous casting solution. Furthermore, it is evident that the mangiferin loading can be increased without affecting the isotropic state of the initial casting solution. Thus, PES/PVP/mangiferin blends may be less affected by concentration changes than PA/PVP/mangiferin in the membrane formation process. While the ternary phase diagram is complex, the crystalline phase of mangiferin may retain its phytochemical properties longer relative to the isotropic amorphous phase. Thus, the presence of mangiferin crystals may render an added a prolonged time release in drug delivery.

Figure 13:
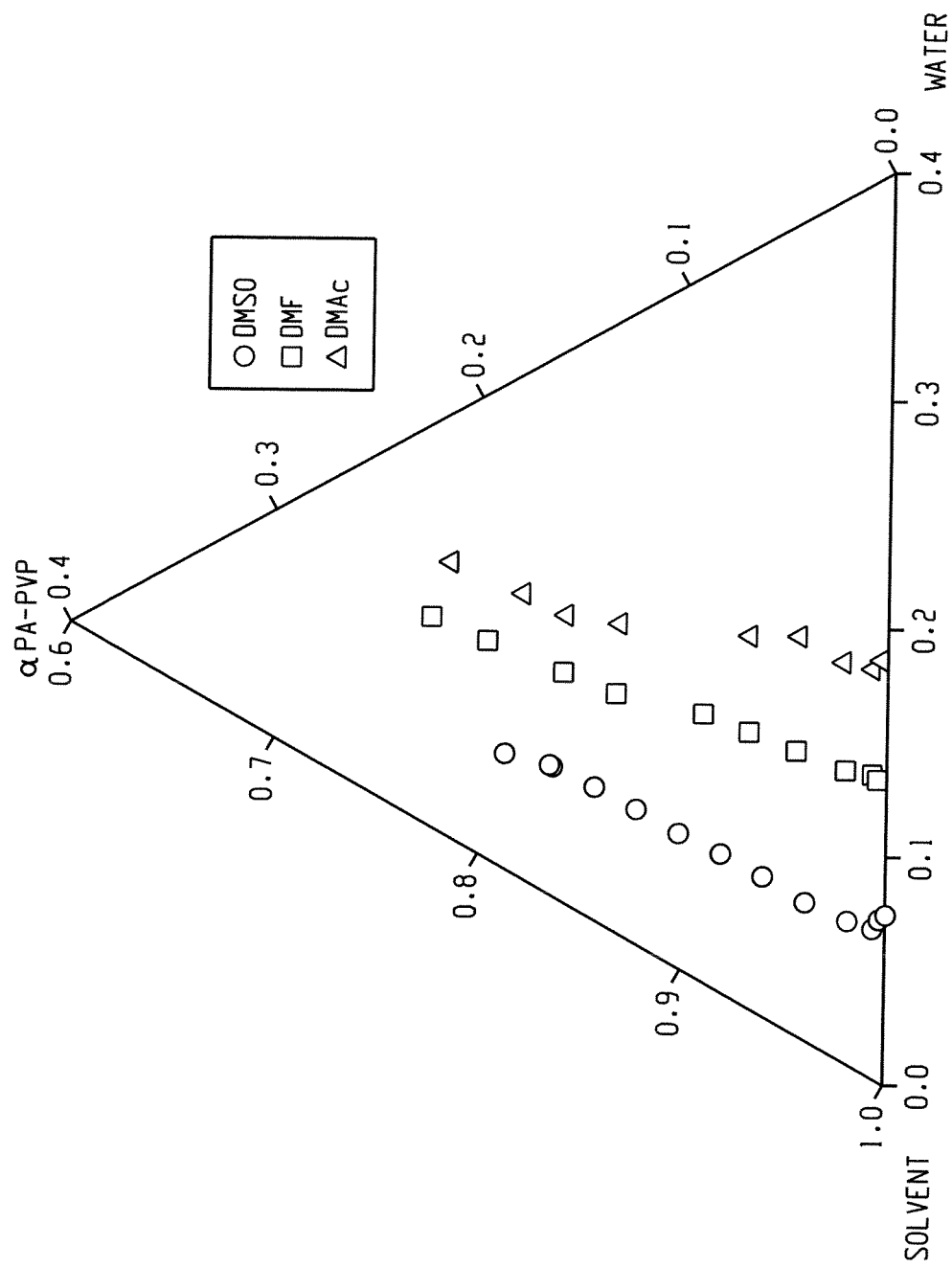
FIG. 13 is a ternary phase diagram for 50-50 polyamide/polyvinylpyrrolidone blend/solvent/water constructed with dimethyl sulfoxide (DMSO), dimethyl formamide (DMF), and dimethylacetamide (DMaC) solvents.

50-50 PA/PVP blends were prepared using dimethylsulfoxide, dimethylformamide, and dimethylacetamide. FIG. 13 is a ternary phase diagram illustrating the phases for PA/PVP blends formed in each solvent with water acting as a non-solvent. In FIG. 13, as the curves for the 50-50 PA/PVP blends shift toward the higher non-solvent (right) side of the triangle, as the solvent quality to the PA/PVP blends improves in the following sequence dimethylacetamide>dimethylformamide>dimethylsulfoxide (i.e., dimethylacetamide has the highest solvent quality). Higher solvent quality is exhibited when the polymer solution remains in a single phase at higher concentrations of non-solvent. Poor solvent quality is exhibited when the polymer solution phase separates even at lower concentrations of non-solvent. However, dimethylsulfoxide was selected as a solvent along with water as non-solvent in subsequent studies due to their proven pharmacologically benign properties.

Morphology Analysis of a Polyamide/Polyvinylpyrrolidone Blend

Membrane morphologies were analyzed as a function of polymer concentration, PA/PVP blend ratio, PES/PVP blend ratio, solvent and exposure to humidity. Different morphologies were observed, depending on these factors, such as sponge-like and finger-like morphologies. In general, the sponge-like structure consists of a dense skin with progressively increasing pore size in the thickness direction, whereas the finger-like structure originates from the skin layer (i.e., the layer that first contacts with the non-solvent upon immersion) and extends through the whole cross-section of the membrane.

Finger-like structures were obtained by faster solvent/non-solvent exchange and phase separation rates, which in turn can be affected by lowering polymer concentration of the blends containing larger amounts of at least one of a polyamide or a polyethersulfone and by using a different solvent of better quality. On the other hand, the sponge-like structures were an outcome of slow solvent/non-solvent exchange and phase separation rates, which can be controlled by increasing polymer concentration of the blends having higher polyvinylpyrrolidone content and by using a solvent of poor quality. It was demonstrated that skin layer morphology can be tailored to be dense or porous. The dense layers were a result of phase separation at a higher polymer concentration and a faster rate of solvent outflow relative to the non-solvent inflow and vice versa. The porous structure consists of a polymer-rich phase, which forms the matrix and a polymer-poor phase which after removal in the coagulation bath become the pores.

The invention claimed is:

1. A dialyzer filter unit comprising a semi-permiable membrane housed within the dialyzer filter unit, the semi-permiable membrane comprising:
   a matrix material; and
   at least one xanthone at least partially dispersed in the matrix material.

2. The dialyzer filter unit of claim 1, wherein the matrix material is selected from the group consisting of polyamides, polyvinylpyrrolidones, polycarbonates, polysulfones, polyacrylonitriles, and combinations thereof.

3. The dialyzer filter unit of claim 2, wherein the matrix material comprises a polysulfone, the polysulfone comprising a polyethersulfone.

4. The dialyzer filter unit of claim 1, wherein the matrix material comprises a blend comprising a polyvinylpyrrolidone and at least one of a polyamide and a polyethersulfone.

5. The dialyzer filter unit of claim 4, wherein the at least one of a polyamide and a polyethersulfone constitutes at least 5% by weight of the blend.

6. The dialyzer filter unit of claim 1, wherein the composition is a solid at room temperature.

7. The dialyzer filter unit of claim 1, wherein the xanthone is hydroxylated.

8. The dialyzer filter unit of claim 1, wherein the xanthone has a structure represented by Structure 11:

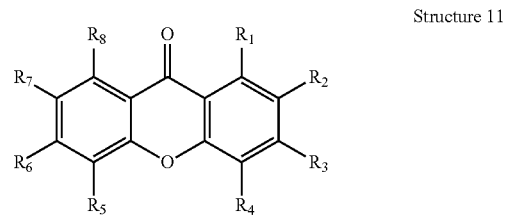

Structure 11 where $R_1$, $R_2$, $R_3$, $R_4$, $R_5$, $R_6$, $R_7$, and $R_8$ are independently selected from H, OH and glycosyl and at least one of $R_1$, $R_2$, $R_3$, $R_4$, $R_5$, $R_6$, $R_7$ and $R_8$ is OH.

9. The dialyzer filter unit of claim 1, wherein the xanthone comprises a glycosylated xanthone.

10. The dialyzer filter unit of claim 9, wherein the glycosylated xanthone comprises 1,3,6,7-tetrahydroxyxanthone-C2-β-D-glycoside (mangiferin).

11. The dialyzer filter unit of claim 1, wherein the xanthone comprises a non-glycosylated xanthone selected from the group consisting of 1,3,6,7-tetrahydroxyxanthone, 1,3-dihydroxyxanthone, 1,6-dihydroxyxanthone, 1,3,7-trihydroxyxanthone, 1,3,5,6-tetrahydroxyxanthone, 2,3,6,7-tetrahydroxyxanthone, 3,4,5,6-tetrahydroxyxanthone, and combinations thereof.

12. The dialyzer filter unit of claim 1, wherein the xanthone constitutes at least 1% by weight of the polymer composition.

13. The dialyzer filter unit of claim 1, wherein the xanthone is dispersed throughout the matrix material.

14. The dialyzer filter unit of claim 1, wherein the membrane is in the form of at least one of a thin film and fibers.

15. The dialyzer filter unit of claim 1, wherein the membrane comprises a bundle of hollow fibers.

16. A method of forming a dialyzer filter comprising:
   forming a membrane comprising a matrix material; and
   at least one xanthone at least partially dispersed in the matrix material; and inserting the membrane into a housing of a dialyzer filter.

17. A method of removing free radicals from a fluid comprising:
filtering a fluid with the dialyzer filter of claim 1, whereby free radicals in the fluid are removed by the membrane.

18. A method for hemodialysis or hemofiltration comprising contacting blood with a dialyzer filter of claim 1.

19. The method of claim 16, where the method of forming the membrane includes forming the biocompatible polymer composition of claim 1, comprising the step of:
combining a matrix material for forming a polymer matrix and at least one xanthone to form a mixture.

20. The method of claim 19, wherein combining the matrix material and at least one xanthone is carried out in the presence of a solvent.

21. The method of claim 20, wherein the solvent includes at least one of dimethylsulfoxide, dimethylacetamide, and dimethylformamide.

22. The method of claim 20, wherein the combining includes combining the matrix material, xanthone, and solvent to form a liquid blend.

23. The method of claim 22, wherein the matrix material and xanthone together constitute at least 1% by weight of the liquid blend.

24. The method of claim 22, wherein the method further comprises immersing the liquid blend into a non-solvent to solidify the biocompatible polymer.

25. The method of claim 22, wherein the method further includes forming fibers from the liquid blend.

26. A dialyzer filter unit comprising a semi-permiable membrane
housed within the the dialyzer filter unit, the semi-permiable membrane comprising:
a matrix material; and
at least one anti-oxidant which is held within the matrix material by hydrogen bonding and wherein the anti-oxidant comprises a xanthone.

27. The dialyzer filter unit of claim 1, wherein at least one xanthone is defined by the by Structure 11:

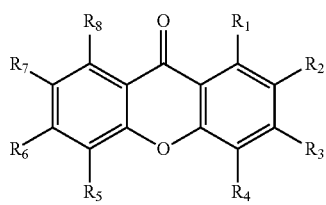

Structure 11 where $R_1$, $R_2$, $R_3$, $R_4$, $R_5$, $R_6$, $R_7$, and $R_8$ are independently selected from H and OH and at least one of $R_1$, $R_2$, $R_3$, $R_4$, $R_5$, $R_6$, $R_7$ and $R_8$ is OH.

* * * * *